(12) United States Patent
Katz et al.

(10) Patent No.: US 8,772,764 B2
(45) Date of Patent: Jul. 8, 2014

(54) ELECTRO-CHEMICAL SENSORS, SENSOR ARRAYS AND CIRCUITS

(71) Applicant: The Johns Hopkins University, Baltimore, MD (US)

(72) Inventors: Howard E. Katz, Owings Mill, MD (US); Hoyoul Kong, Timonium, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/725,630

(22) Filed: Dec. 21, 2012

(65) Prior Publication Data
US 2013/0161599 A1    Jun. 27, 2013

Related U.S. Application Data

(60) Provisional application No. 61/580,496, filed on Dec. 27, 2011.

(51) Int. Cl.
*H01L 29/08*     (2006.01)

(52) U.S. Cl.
USPC ...... 257/40; 257/253; 257/E51.001; 257/E51.027

(58) Field of Classification Search
USPC .................. 257/40, 253, E51.001, E51.027
See application file for complete search history.

(56) References Cited

U.S. PATENT DOCUMENTS

| | | | |
|---|---|---|---|
| 6,905,834 B1* | 6/2005 | Simpson et al. | 435/7.32 |
| 2009/0181509 A1* | 7/2009 | Pan et al. | 438/293 |
| 2013/0075690 A1* | 3/2013 | Briman et al. | 257/9 |

OTHER PUBLICATIONS

Ai"ch et al., Chem. Mater. 2009, 21, 751.
Arias et al., Chem. Rev. 2010, 110, 3.
Aziz et al., Adv. Mater. 2007, 19, 3257.
Ba"uerle et al., Adv. Mater. 1993, 5, 848.
Ba"uerle et al., Synth. Met. 1993, 61, 71.
Ballarin et al., Electroanal. Chem. 1998, 449, 173.
Barik et al., Macromolecules 2008, 41, 6376.
Beaujuge et al., J Am. Chem. Soc. 2011, 133, 20009.
Besbes et al., Adv. Mater. 2001, 13, 1249.
Blouin et al., Macromol. Chem. Phys. 2006, 207, 175.
Brem et al., Tet Asymmetry 2011, 22, 315.
Bryce et al., Nature 1984, 309, 119.
Bryce et al., Synth. Met. 1991, 39, 397.
Carrasco et al., Surf. Interface Anal. 2007, 39, 26.
Chang et al., J AppL Phys. 2006, 100, 014506.
Cheng et al., Chem. Rev. 2009, 109, 5868.
Crone et al., Appl. Phys. Lett. 2001, 78, 2229.
Dimitrakopoulos et al., Adv. Mater. 2002, 14, 99.

(Continued)

*Primary Examiner* — Andy Huynh
(74) *Attorney, Agent, or Firm* — Venable LLP; Henry J. Daley

(57) ABSTRACT

An electro-chemical sensor includes a first electrode, a second electrode spaced apart from the first electrode, and a semiconductor channel in electrical contact with the first and second electrodes. The semiconductor channel includes a trapping material. The trapping material reduces an ability of the semiconductor channel to conduct a current of charge carriers by trapping at least some of the charge carriers to localized regions within the semiconductor channel. The semiconductor channel includes at least a portion configured to be exposed to an analyte to be detected, and the trapping material, when exposed to the analyte, interacts with the analyte so as to at least partially restore the ability of the semiconductor channel to conduct the current of charge carriers.

19 Claims, 31 Drawing Sheets

(56) References Cited

OTHER PUBLICATIONS

Du et al., Pro. Polym. Sci. 2012, 37, 820.
Dubey et al., Polym. Sci. Part B: Polym. Phys. 2011, 49, 467.
Facchetti, A. Mater. Today 2007, 10, 28.
Facchetti, Chem. Mater. 2011, 23, 733-758.
Forrest, S. R. Nature 2004, 428, 911.
Friend et al., Nature 1999, 397, 121.
Fujinami et al., ACS Macro. Lett. 2012, 1, 67.
Garin et al., Synthesis 1994, 5, 489.
Gautier et al., Macromolecules 1993, 26, 4094.
Gunes et al., Chem. Rev. 2007, 107, 1324.
He et al., Macromolecules 2008, 41, 9760.
Hiroshige et al., Synth. Met. 2006, 156, 1341.
Hiroshige et al., Synth. Met. 2007, 157, 467.
Huang et al., Adv Mater 2008, 20, 2567.
Huang et al., Chem-Eur J. 2006, 12, 607.
Huang et al., J Am Chem Soc 2007, 129, 9366.
Huang et al., J Mater Chem 2010, 20, 2644.
Huchet et al., 1 Phys. Chem. B 1998, 102, 7776.
Huchet et al., Adv. Mater. 1998, 10, 541.
Kemp et al., J Polym. Sci. Part B: Polym. Phys. 1999, 37, 953.
Kong et al., Chem. Mater. 2012, 24, 2621.
Lee et al., Chem. Rev. 2001, 101, 2869.
Levesque et al., Chem. Mater. 2007, 19, 2128.
Li et al., Appl. Phys. Lett. 2005, 86, 042105.
Li et al., Macromolecules 2002, 35, 6900.
Liedberg et al., J Phys. Chem. B 1997, 101, 5951.
Lo et al., Chem. Rev. 2007, 107, 1097.
Lu et al., Chin. Phys: Lett. 2010, 27, 057201.
Lu et al., Macromolecules 2005, 38, 8494.
Lyskawa et al., Am. Chem. Soc. 2004, 126, 12194.
Maddison et al., Synth. Met. 1988, 26, 99.
Magnoni et al., Acta. Polym. 1996, 47, 228.
Marsella et al., *J. Am. Chem. Soc.* 1993, 115, 12214.
Masubuchi et al., *Synth. Met.* 1993, 57, 4962.
Mateeva et al., *J Appl. Phys.* 1998, 83, 3111.
McQuade et al., *Chem. Rev.* 2000, 100, 2537.
Mishra et al., *Chem. Rev.* 2009, 109, 1141.
Nie et al., *Nat. Mater.* 2007, 6, 609.
Olenyuk et al., *J. Nature* 1999, 398, 796.
Ong et al., *J Am Chem Soc* 2004, 126, 3378.
Operamolla, et al., *Eur. J Org. Chem.* 2011, 423-450.
Osaka et al., Acc. Chem. Res. 2008, 41,1202.
Park et al., Synth. Met. 1991, 41, 27.
Park, Y. W. Synth. Met. 1991, 45, 173.
Poehler et al., Energy Environ. Sci. 2012, 5, 8110.
Pukacki et al., Synth. Met. 1994, 62, 253.
Purcell et al., J Am. Chem. Soc. 1994, 116, 11985.
Roncali et al., Synth. Met. 1990, 36, 267.
Royer et al., Sens. Actuat. B 2011, 158, 333.
Scheib et al., J Mater. Chem. 1999, 9, 2139.
See et al., Adv Mater 2007, 19, 3322.
Sun et al., Macromolecules 2010, 43, 2897.
Swager et al., J. Adv. Mater. 1994, 6, 595.
Swager et al., Polym. Prep. 1994, 35, 206.
Taniguchi et al., J. Mater. Chem. 2006, 16, 3459.
Thompson et al., Angew. Chem., Int. Ed. 2008, 47, 58.
Torsi et al., J Phys Chem B 2003, 107, 7589.
Torsi et al., Org Electron 2009, 10, 233.
Toshima, N. Macromol. Symp. 2002, 186, 81.
Tour et al., J. Am. Chem. Soc. 1995, 117, 9529.
Tremblay et al., Adv. Funct. Mater. 2011, 21 4314.
Vigalok et al., Am. Chem. Soc. 2001, 123, 7917.
Wakim et al., Polym. Rev. 2008, 48, 432.
Wen et al., Adv. Mater. 2010, 22, 1331.
Xuan et al., Phys. Rev. Part B 2010, 82, 115454.
Yakuphanoglu et al., J Phys. Chem. C 2007, 111, 1840.
Yamashita et al., J. Mater. Chem., 1998, 8(9), 1933-1944.
Yan et al., Therm. Anal. Calorim. 2002, 69, 881.
Zahn et al., Angew. Chem., Int. Ed. 2002, 41, 4225.
Zhu et al., Appl. Phys. Lett. 2002, 81, 4643.
Zuzok et al., J Chem. Phys. 1991, 95, 1270.

\* cited by examiner

Table 4. Power Factor of P1 doped with F4TCNQ

| F4TCNQ μL (0.5 mg/mL) | Power Factor (μW/mK²) |
|---|---|
| 30 | - |
| 40 | $1.93 \times 10^{-4}$ |
| 50 | $2.20 \times 10^{-4}$ |
| 60 | $2.33 \times 10^{-4}$ |
| 70 | $9.27 \times 10^{-4}$ |
| 80 | $2.63 \times 10^{-3}$ |
| 90 | $6.49 \times 10^{-3}$ |

Table 5. Power Factor of P2 doped with F4TCNQ

| F4TCNQ μL (0.5 mg/mL) | Power Factor (μW/mK²) |
|---|---|
| 0 | - |
| 30 | $2.56 \times 10^{-4}$ |
| 40 | $4.19 \times 10^{-4}$ |
| 50 | $3.49 \times 10^{-4}$ |
| 70 | $3.80 \times 10^{-3}$ |
| 90 | $1.02 \times 10^{-3}$ |

Table 6. Power Factor of P3 doped with F4TCNQ

| F4TCNQ μL (0.5 mg/mL) | Power Factor (μW/mK²) |
|---|---|
| 50 | $1.81 \times 10^{-5}$ |
| 60 | $1.03 \times 10^{-3}$ |
| 70 | $2.03 \times 10^{-3}$ |
| 80 | $1.54 \times 10^{-3}$ |
| 90 | $5.34 \times 10^{-4}$ |

Table 7. Power Factor of P1 doped with NOPF6

| Dipped in NOPF6 Time (min) | Power Factor (μW/mK²) |
|---|---|
| 1 | - |
| 2 | - |
| 3 | - |
| 4 | $2.96 \times 10^{-4}$ |
| 5 | $1.35 \times 10^{-3}$ |
| 7 | $5.06 \times 10^{-3}$ |
| 9 | $1.28 \times 10^{-2}$ |
| 11 | $3.34 \times 10^{-2}$ |
| 13 | $1.59 \times 10^{-3}$ |
| 15 | $4.38 \times 10^{-2}$ |

Table 8. Power Factor of P3 doped with NOPF6

| Dipped in NOPF6 Time (min) | Power Factor (μW/mK²) |
|---|---|
| 1 | - |
| 2 | $7.26 \times 10^{-4}$ |
| 3 | $1.59 \times 10^{-2}$ |
| 4 | $1.62 \times 10^{-2}$ |
| 5 | $6.4 \times 10^{-2}$ |
| 7 | $10.4 \times 10^{-2}$ |
| 9 | $10.8 \times 10^{-2}$ |
| 11 | $13.8 \times 10^{-2}$ |
| 13 | $7.4 \times 10^{-2}$ |
| 15 | $6.1 \times 10^{-2}$ |

FIG. 22

ELECTRO-CHEMICAL SENSORS, SENSOR ARRAYS AND CIRCUITS

CROSS-REFERENCE OF RELATED APPLICATION

This application claims priority to U.S. Provisional Application No. 61/580,496 filed Dec. 27, 2011, the entire content of which is hereby incorporated by reference.

This invention was made with Government support of Grant No. DE-FG02-07ER46465, awarded by the Department of Energy, Office of Basic Energy Sciences. The U.S. Government has certain rights in this invention.

BACKGROUND

1. Field of Invention

The field of the currently claimed embodiments of this invention relates to electro-chemical sensors, and more particularly to electro-chemical sensors that have analyte-responsive semiconductors.

2. Discussion of Related Art

In recent years, various chemical sensors based on organic field effect transistors (OFETs) have been proposed and investigated, as they possess advantages of easy tuning of the chemical and physical properties, low-cost processing, and flexible mechanical properties.[1,2] Most OFETs exposed to various chemical compounds such as polar solvents including water vapor, and particularly, nitroaromatic explosives, showed decreased output current and mobility.[1,3-11] The degradation of the transistor performance by exposure to the chemical compounds was caused by reduced charge transport dipoles causing charge trapping at grain boundaries.[1,5]

However, even though many organic semiconductors have been shown to result in current decreases when environmental agents contact them as voltage is applied, they have limited specificity since the responses are similar. Also, the absolute current level is limited to the non-exposed state. There thus remains a need for improved electro-chemical sensors.

References for Background Section (1) See, K. C.; Becknell, A.; Miragliotta, J.; Katz, H. E. *Adv Mater* 2007, 19, 3322.

(2) Torsi, L.; Tanese, M. C.; Cioffi, N.; Gallazzi, M. C.; Sabbatini, L.; Zambonin, P. G.; Raos, G.; Meille, S. V.; Giangregorio, M. M. *J Phys Chem B* 2003, 107, 7589.

(3) Huang, J.; Miragliotta, J.; Becknell, A.; Katz, H. E. *J Am Chem Soc* 2007, 129, 9366.

(4) Huang, J.; Sun, J.; Katz, H. E. *Adv Mater* 2008, 20, 2567.

(5) Huang, J.; Dawidczyk, T. J.; Jung, B. J.; Sun, J.; Mason, A. F.; Katz, H. E. *J Mater Chem* 2010, 20, 2644.

(6) Royer, J. E.; Lee, S.; Chen, C.; Ahn, B.; Trogler, W. C.; Kanicki, J.; Kummel, A. C. *Sensor Actuat B-Chem* 2011, 158, 333.

(7) Zhu, Z. T.; Mason, J. T.; Dieckmann, R.; Malliaras, G. G. *Appl Phys Lett* 2002, 81, 4643.

(8) Li, D. W.; Borkent, E. J.; Nortrup, R.; Moon, H.; Katz, H.; Bao, Z. N. *Appl Phys Lett* 2005, 86.

(9) Crone, B.; Dodabalapur, A.; Gelperin, A.; Torsi, L.; Katz, H. E.; Lovinger, A. J.; Bao, Z. *Appl Phys Lett* 2001, 78, 2229.

(10) Chang, J. B.; Liu, V.; Subramanian, V.; Sivula, K.; Luscombe, C.; Murphy, A.; Liu, J. S.; Frechet, J. M. J. *J. Appl. Phys.* 2006, 100.

(11) Torsi, L.; Marinelli, F.; Angione, M. D.; Dell'Aquila, A.; Cioffi, N.; De Giglio, E.; Sabbatini, L. *Org Electron* 2009, 10, 233.

SUMMARY

An electro-chemical sensor according to an embodiment of the current invention includes a first electrode, a second electrode spaced apart from the first electrode, and a semiconductor channel in electrical contact with the first and second electrodes. The semiconductor channel includes a trapping material. The trapping material reduces an ability of the semiconductor channel to conduct a current of charge carriers by trapping at least some of the charge carriers to localized regions within the semiconductor channel. The semiconductor channel includes at least a portion configured to be exposed to an analyte to be detected, and the trapping material, when exposed to the analyte, interacts with the analyte so as to at least partially restore the ability of the semiconductor channel to conduct the current of charge carriers.

An electro-chemical sensor array according to an embodiment of the current invention includes a plurality of electro-chemical sensor elements. At least one electro-chemical sensor element of the plurality of electro-chemical sensor elements includes a first electrode, a second electrode spaced apart from the first electrode, and a semiconductor channel in electrical contact with the first and second electrodes. The semiconductor channel includes a trapping material. The trapping material reduces an ability of the semiconductor channel to conduct a current of charge carriers by trapping at least some of the charge carriers to localized regions within the semiconductor channel. The semiconductor channel includes at least a portion configured to be exposed to an analyte to be detected, and the trapping material, when exposed to the analyte, interacts with the analyte so as to at least partially restore the ability of the semiconductor channel to conduct the current of charge carriers.

An electrical circuit according to an embodiment of the current invention includes an electro-chemical sensor element. The electro-chemical sensor element includes a first electrode, a second electrode spaced apart from the first electrode, and a semiconductor channel in electrical contact with the first and second electrodes. The semiconductor channel includes a trapping material. The trapping material reduces an ability of the semiconductor channel to conduct a current of charge carriers by trapping at least some of the charge carriers to localized regions within the semiconductor channel. The semiconductor channel includes at least a portion configured to be exposed to an analyte to be detected, and the trapping material, when exposed to the analyte, interacts with the analyte so as to at least partially restore the ability of the semiconductor channel to conduct the current of charge carriers.

BRIEF DESCRIPTION OF THE DRAWINGS

Further objectives and advantages will become apparent from a consideration of the description, drawings, and examples.

FIG. 22 provides data in Tables 4-6.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Figure 1:
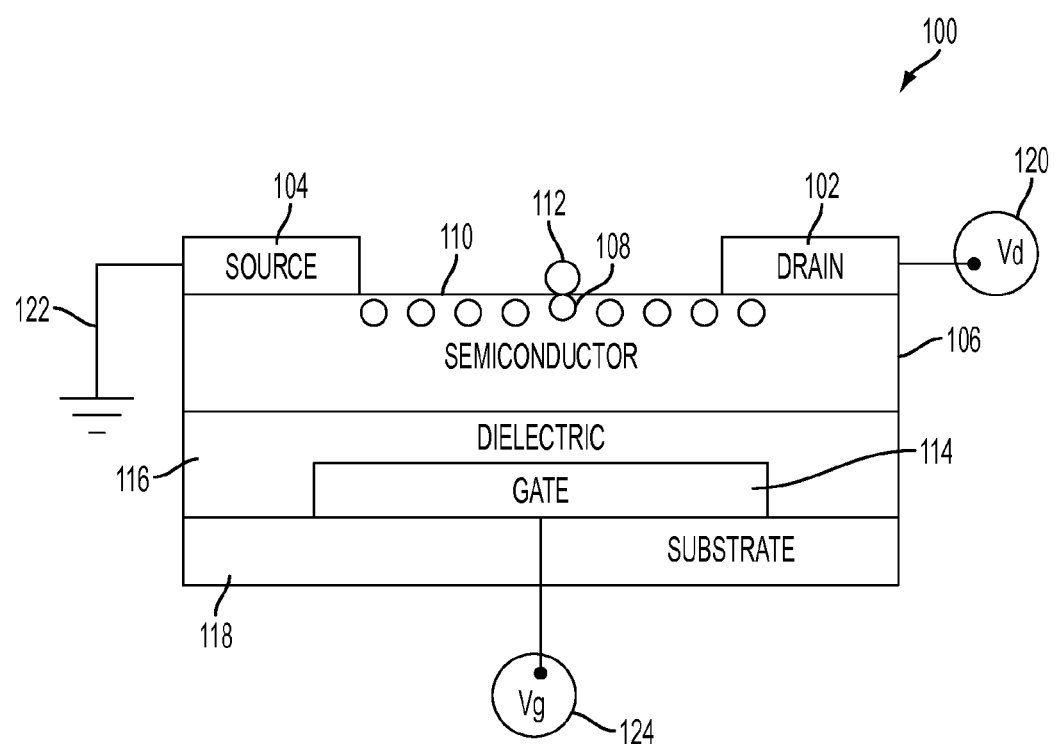
FIG. 1 is a schematic illustration of an electro-chemical sensor according to an embodiment of the current invention.

FIG. 1 is a schematic illustration of an electro-chemical sensor 100 according to an embodiment of the current invention. The electro-chemical sensor 100 includes a first electrode 102, a second electrode 104 spaced apart from the first electrode 102, and a semiconductor channel 106 in electrical contact with the first and second electrodes (102, 104). The semiconductor channel 106 includes a trapping material 108 that reduces an ability of the semiconductor, channel 106 to conduct a current of charge carriers by trapping at least some of said charge carriers to localized regions within the semiconductor channel 106. The semiconductor channel 106 includes at least a portion 110 configured to be exposed to an analyte 112 to be detected. The trapping material 108, when exposed to the analyte 112, interacts with the analyte 112 so as to at least partially restore the ability of the semiconductor channel 106 to conduct the current of charge carriers.

In some embodiments, the semiconductor channel 106 can include a p-type semiconductor such that the charge carriers are holes. In this case, trapping material 108 can be an electron donor material and the analyte 112 can be an electron acceptor material. In some embodiments, the semiconductor channel 106 can include an n-type semiconductor such that the charge carriers are electrons. In this case, the trapping material 108 can be an electron acceptor material and the analyte can be an electron donor material.

In some embodiments, the semiconductor channel 106 can include an organic semiconductor. In some embodiments, the trapping material 108 can be dispersed within the organic semiconductor. In further embodiments, the trapping material 108 can also be an organic material. In some embodiments, the organic semiconductor can be, or can include, a small molecule organic semiconductor. In further embodiments, the organic semiconductor can be, or can include, an organic polymer semiconductor. In some embodiments, the trapping material 108 can be covalently attached to the organic polymer semiconductor.

In some embodiments, the electro-chemical sensor 100 can further include a third electrode 114 arranged proximate the semiconductor channel 106 to expose at least a portion to the semiconductor channel 106 to a controllable electric field such that the first, second and third electrodes (102, 104, 114)

and the semiconductor channel 106 together provide a field effect transistor. In some embodiments, the electro-chemical sensor 100 can further include a dielectric layer 116 disposed between the third electrode 114 and the semiconductor channel 106. In some embodiments, the electro-chemical sensor 100 can further include a substrate 118 upon which the semiconductor channel 106, the first electrode 102, and the second electrode 104 are formed. The substrate 118 can be, but is not limited to, a flexible substrate, for example.

Although the embodiment of an electro-chemical sensor 100 illustrated in FIG. 1 is a field effect transistor, the concepts of the current invention are not limited to that particular structure of a transistor. Furthermore, two terminal electrochemical sensors are also within the scope of the current invention. For example, with two electrodes, the electro-chemical sensor 100 can operate effectively as a variable resister in which the resistance changes due to exposure to the analyte. The electro-chemical sensor 100 can be, but is not limited to, a thin device, for example. The electro-chemical sensor 100 can be a more complex device that includes additional electronic and/or electro-chemical elements. For example, the electro-chemical sensor 100 can be connected in a circuit that includes a voltage source 120 and ground 122. It can further include a voltage source 124 for controlling a gate voltage, for example, in the case in which the third electrode 114 is a gate electrode. Furthermore, the electro-chemical sensor 100 can include additional layers in its structure as well as packaging structures, etc.

A wide range of materials can be used in the electro-chemical sensor 100, depending on the particular application. For example, Yamashita et al., J. Mater. Chem., 1998, 8(9), 1933-1944 (the entire content of which is incorporated herein by reference) described a large number of donor-acceptor compounds that could be used as trapping materials and analytes for particular applications according to some embodiments of the current invention. However, the broad concepts of the current invention are not limited to these particular examples. Operamolla, et al., *Eur. J. Org. Chem.* 2011, 423-450 (the entire content of which is incorporated herein by reference) describe some examples of organic semiconductors that can be used according to some embodiments of the current invention. However, the broad concepts of the current invention are not limited to these particular examples. A. Facchetti, Chem. Mater. 2011, 23, 733-758 (the entire content of which is incorporated herein by reference) describe some examples of organic polymeric semiconductors that can be used according to some embodiments of the current invention. However, the broad concepts of the current invention are not limited to these particular examples.

In operation, the blocking material 108 causes the conductivity of the semiconductor channel 106 to decrease. For example, in the case of a p-type semiconductor, the introduction of an electron donor material provides reactive sites that interact with the charge carriers (holes in this case) thus acting to reduce the ability of the p-type semiconductor to conduct a current of holes. In the case of an n-type semiconductor, the charge carriers are electrons, and thus the introduction of an electron acceptor as the trapping material. One can select particular semiconductors and blocking materials to obtain the degree of reduction in current needed for a particular application. In the embodiments in which the trapping material and analyte are donor acceptor pairs, the analyte interacts with the blocking material to neutralize the trapping effect. A surface of the semiconducting channel 106 of the electro-chemical sensor 100 can be configured such that the analyte can be brought into contact with it, for example.

Depending on the particular applications, and the corresponding materials selected, a wide range of manufacturing methods can be used to produce the electro-chemical sensor 100. These can include, but are not limited to, printing methods, spin coating, doctor blading and/or roll-to-roll processing, for example.

Some embodiments can include arrays of the electro-chemical sensor elements. These can be arranged in regular and/or irregular patterns and are not limited to a particular number in the array. Also, the elements in the array can be the same, or different. For example, different elements in the array can have the same or different semiconductor and/or trapping materials. This can allow the array to be sensitive to one or more analytes. In addition, one or more elements in the array can be constructed without a trapping material. This can be useful for cases in which the analyte of interest causes a decrease in conductivity of a semiconductor channel that does not have a trapping material, while the same semiconductor channel that includes the trapping material experiences an increase in conductivity due to exposure to the analyte. This can help to further enhance the selectivity to an analyte of interest.

Further additional concepts and embodiments of the current invention will be described by way of the following examples. However, the broad concepts of the current invention are not limited to these particular examples.

EXAMPLE 1

In this example, organic field effect transistors (OFETs) using pure poly(3,3'''-didodecyl quaterthiophene) (PQT12) semiconductor showed decreased current signal after exposure to 2,4,6-trinitrotoluene (TNT) explosive, which is similar to typical OFETs used as sensors. To obtain a unique and useful "turn on" current signal according to an embodiment of the current invention, an electron rich compound, tetrakis (pentylthio)tetrathiafulvalene (TPT-TTF), was blended with the PQT12. The PQT12:TPT-TTF blend devices exposed to very small amounts of TNT analyte showed dramatic current increase. The greatly modified response is attributed to formation of a TNT-TPT-TTF complex as observed by NMR and cyclic voltammetry.

Here, we found the expected current decrease of the poly (3,3'''-didodecyl quaterthiophene) (PQT12) OFETs on exposure to 2,4,6-trinitrotoluene (TNT) explosive. In addition, we fabricated blended PQT12 semiconductor with 1 to 20% tetrakis(pentylthio)tetrathiafulvalene (TPT-TTF) as an electron donating/easily oxidized material. In contrast to pure PQT12 devices, PQT12:TPT-TTF blend devices exposed to TNT analyte showed significant current increase, which we attribute to complexation between TPT-TTF and TNT. The increased current response to TNT exposure of a p-type semiconductor is very rare and useful.[12] The PQT12:10% TPT-TTF blend device exposed to 190 pg TNT/$cm^2$ showed 3000% increased current.

Experimental

Highly conducting n-doped silicon wafer is used as a substrate with a 100-nm or 300-nm thick $SiO_2$ thermal oxide layer. The wafers were cleaned by sonication using acetone and 2-propanol (IPA) and were then treated with hexamethyldisilazane (HMDS). 50-nm-thick gold pads with a 2.5 nm chrome adhesion layer are thermally evaporated to form source and drain contacts. The channel length is L=250 μm and the width is W=8 mm. PQT12 was synthesized according to known procedures.[13] PQT12 alone or blended with 1~20% TPT-TTF solutions (4 mg/ml chlorobenzene) was spin-coated at 1500 rpm/s. All OFETs were fabricated without any post annealing processes, to obtain a rougher surface for larger sensing area. Novec fluoropolymer was painted on the edge of the channel area to create a dam. After that, TNT solution was dropped in the region bounded by the Novec (0.81 cm$^2$). In addition to dropping of the TNT solution, polydimethylsiloxane (PDMS) with TNT solid was also used for delivery of TNT analyte. Finally, IPA solvent was evaporated in air for 10 min. All sensing experiments were done in air.

Results and Discussion

Figures 2A, 2B, 2C, 2D:
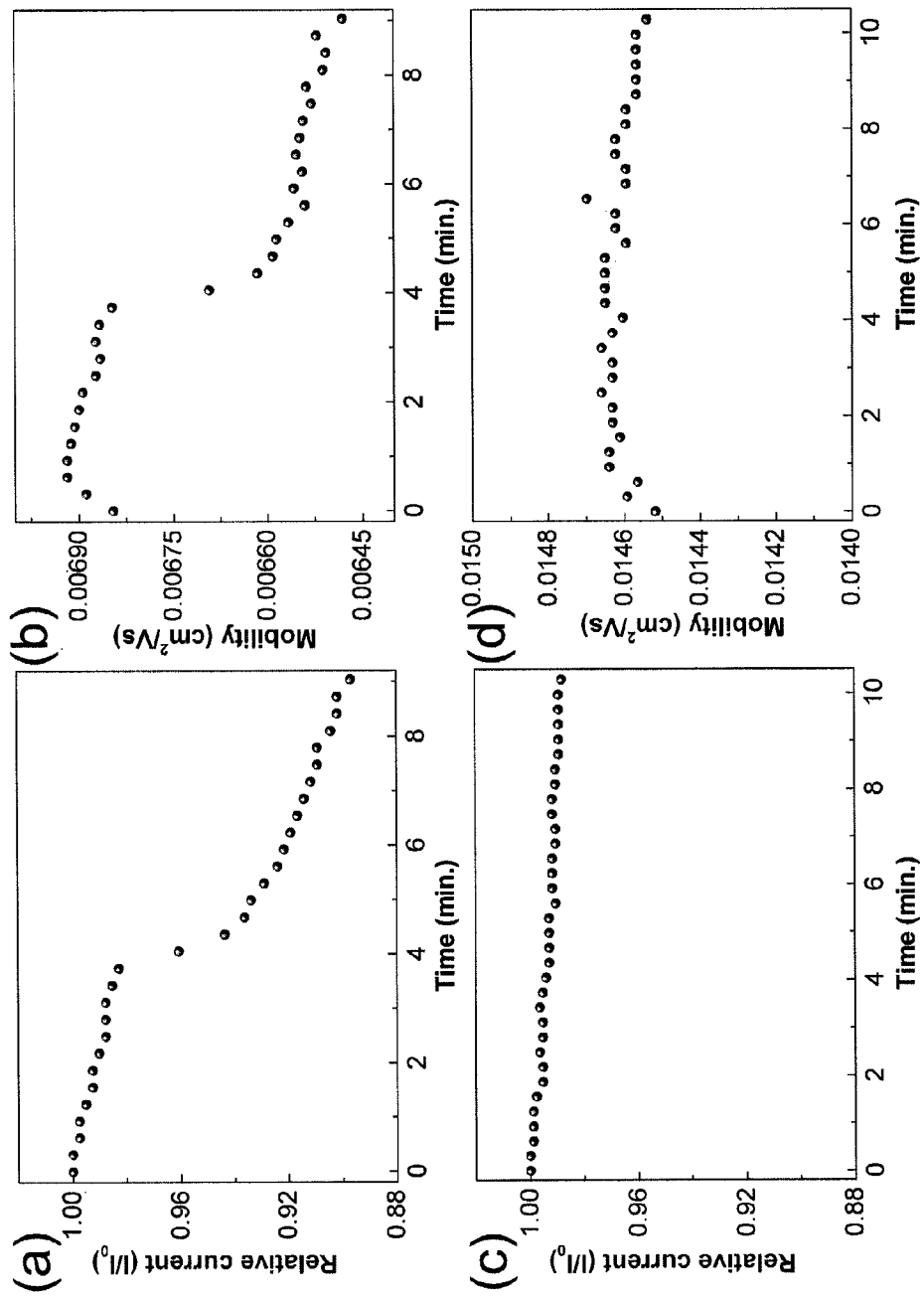
FIGS. 2A-2C show relative transfer curve current change at $V_D = V_G = -40$ V and FIGS. 2B-2D mobility change of PQT12 devices before and after exposure to TNT solid compound using PDMS stamp method at 3.8 minutes. The PQT12 device for (c) and (d) was encapsulated with glass resin 150.

To investigate current changes of PQT12 OFETs exposed to TNT analyte, we stamped the PDMS with TNT solid. 3 μl of 0.1 mg TNT in 1 ml IPA solvent was dropped on 0.2 cm$^2$ PDMS. After evaporation of the IPA solvent, residual TNT solid on PDMS was transferred to the PQT12 layer of the OFET device channel. We measured and extracted the transfer curve current at $V_D=V_G=-40$ V, and mobility of the devices 4 minutes before and after exposure to TNT. The current and mobility was decreased when the TNT was transferred (FIGS. 2A and 2B). Although TNT, an electron withdrawing molecule, diffuses into grain boundaries of the PQT12 film, which in theory could result in thermally assisted doping of the p-channel PQT12 semiconductor, the net response induced by the stronger dipole quenching effect of TNT results in a decrease in source-drain current.[1,3,5] In contrast, the PQT12 device encapsulated with "glass resin 150" insulating polymer does not show current and mobility change after exposure to TNT analyte.

Figures 3A, 3B:
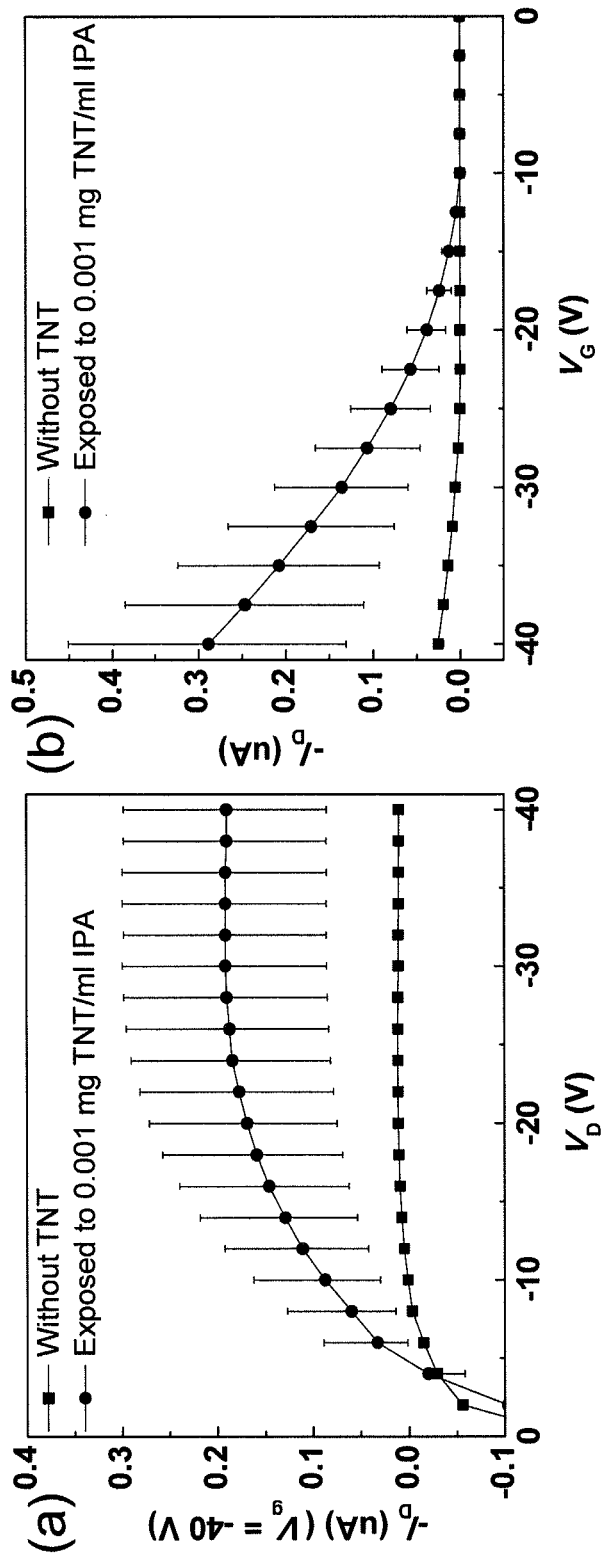
FIG. 3A provides an output curve change at $V_D=V_G=-40$ V and FIG. 3B transfer curve change at $V_D=-40$ V of PQT12: 5% TPT-TTF devices before and after dropping 15 µl of 0.001 mg TNT/ml IPA solution on 0.81 cm² area.
Figure 4:
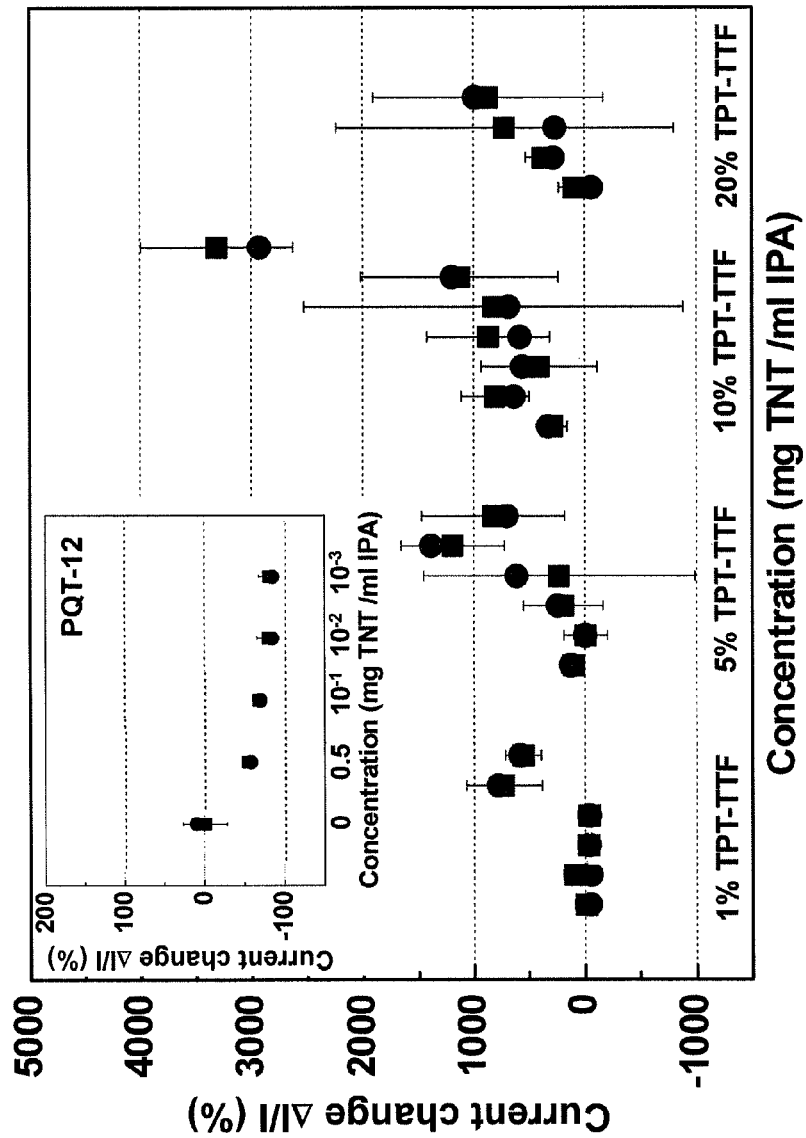
FIG. 4 shows output curve current change $\Delta I/I$ (%) at $V_D=V_G=-40$ V of pure PQT12. device (inset) and blended PQT12 devices with 1~20% TPT-TTF before and after dropping 15 µl of 0, $10^{-1}$, $10^{-2}$, $10^{-3}$, $10^{-4}$, and $10^{-5}$ (left to right) mg TNT/ml IPA solution on 0.81 cm² area. Circle and square show median and mean value, respectively. The bar shows standard deviation.
Figures 5A, 5B:
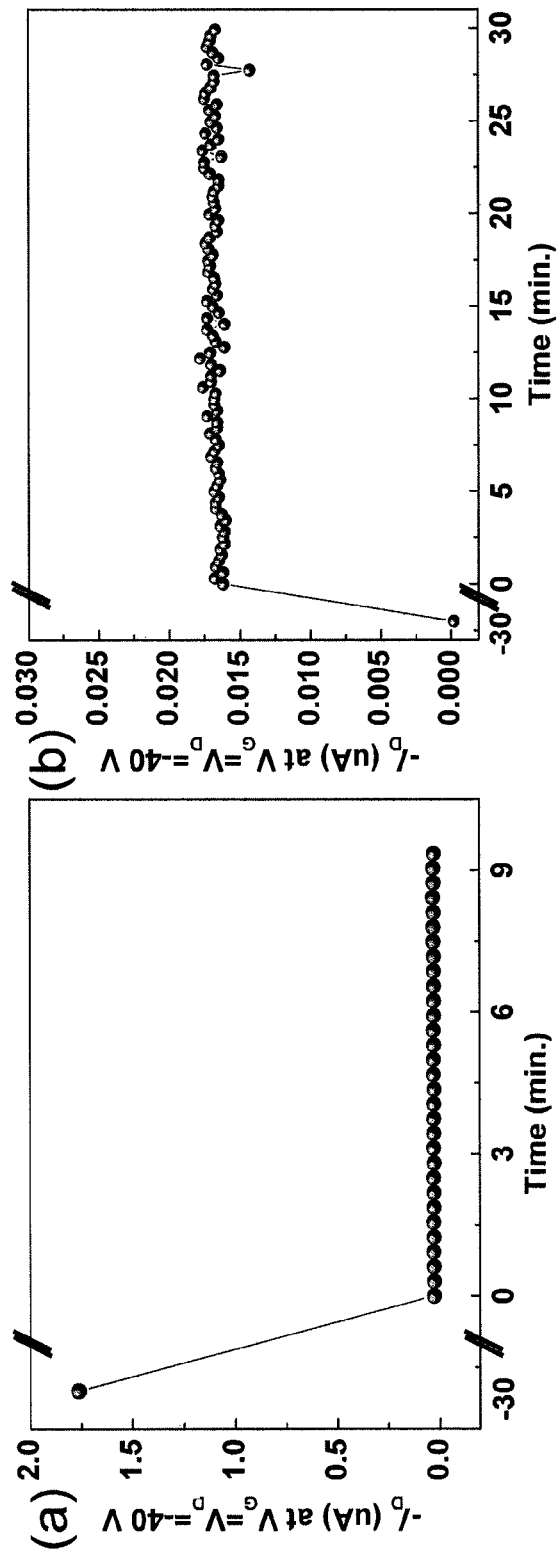
FIGS. 5A-5B show output curve current change of (a) pure PQT12 device and (b) PQT12:10% TPT TTF device at $V_D=V_G=-40$ V. After dropping 15 µl of 0.1 mg TNT/ml IPA solution on 0.81 cm² area, the devices were kept in ambient conditions for 30 minutes to evaporate IPA solvent.
Figures 6A, 6B:
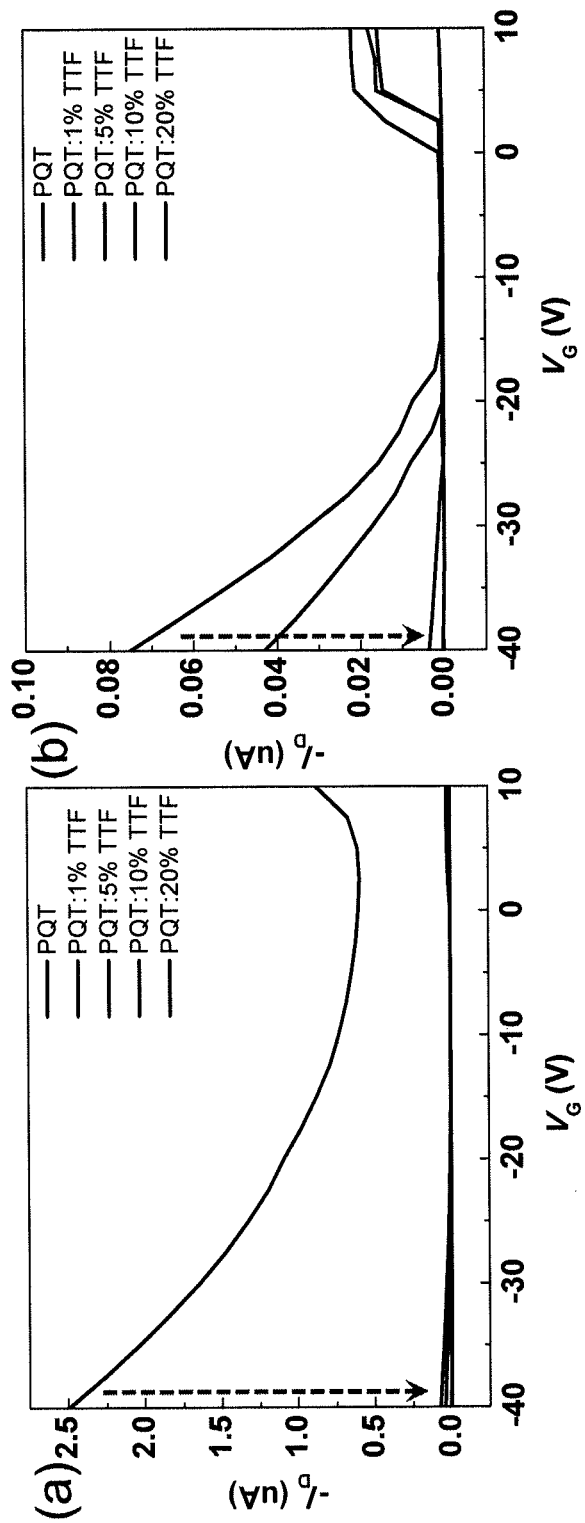
FIG. 6A shows transfer curve at $V_D=-40$ V of pure PQT12 device and blended PQT12 devices with 1~20% TPT-TTF, and FIG. 6B expanded graph of (a).

We then blended PQT12 with 1~20 w % TPT-TTF as an active layer. We checked the basic transfer characteristics of the PQT12:TPT-TTF blend OFET devices (FIGS. 6A-6B). Although a very small amount of TPT-TTF (1%) was added, the current significantly decreased. Further, the current decreased with increasing TPT-TTF addition. The transistor behavior using PQT12 with 5% blended TPT-TTF was investigated (FIGS. 3A-3B). The initial output and transfer current of the blend-based OFET was observed to be very low, at the nA level. After exposure to 10$^{-3}$ mg TNT/IPA solution, both currents were significantly increased to nearly 0.2~0.3 μA. TNT has strong electron withdrawing nitro groups and TPT-TTF is an electron rich material. Thus, it is possible that there is a generation of a new energy level from the interaction of TNT and TPT-TTF, which can help inject more holes, or inhibit hole trapping, of the bulk PQT12 active layer.

To confirm this phenomenon, OFETs with many blend ratios as active layer were prepared and exposed to various concentrations of TNT solutions (10$^{-1}$ to 10$^{-5}$ mg TNT/ml IPA). The TNT solution was dropped on 0.81 cm$^2$ of Novec-bounded channel area. When the pure IPA solvent was dropped and dried on various kinds of pure or blended PQT12 film with TPT-TTF, there were no significant current changes, which mean the IPA solvent as an analyte vehicle does not affect transistor behaviors due to very weak chemical interaction with the semiconducting layer.[11] The pure PQT12 devices exposed to 0.5 to 10$^{-3}$ mg TNT/ml IPA showed decreased current, more so than with TNT stamp tests, because of the penetration of the TNT solution more easily into the PQT12 film than TNT solid itself. The PQT12:1% TPT-TTF blend device showed increased current when the device was exposed to more dilute TNT solution (from 10$^{-3}$ mg TNT/ml IPA). Other TPT-TTF blend devices showed similar tendencies for current change. When higher concentrations of TNT solution were dropped, the current did not show significant change. Also, the blend film mixed with smaller amounts of TPT-TTF showed no current change. However, on increasing the blend ratio, TPT-TTF blend devices showed more increased current after exposure to 10$^{-1}$ mg TNT/ml IPA. More weight percent of TPT-TTF caused increase in current after interacting with TNT analyte. Thus the current increase is more likely due to the formation of complex between TNT and TPT-TTF which competes with current decrease in case of pure TNT. When more dilute TNT solution was exposed to higher TPT-TTF blend film, the current increased drastically. The current changes showed linear dependence on lower concentration of TNT solutions. In the case of 10% TPT-TTF blend device, the current was increased about 3000% after exposure to 10$^{-5}$ mg TNT/ml IPA. To the best our knowledge, the current change is the best. The actual TNT amount transferred to the active layer is less than 190 pg TNT/cm$^2$.

To check the persistence of the TNT response, pure PQT12 and PQT12:10% TPT-TTF blend devices were measured before and after dropping 0.1 mg TNT/ml IPA and then kept in ambient conditions for 30 minutes, followed by measurement for 10 to 30 minutes. After exposure to the TNT solutions, the pure PQT12 device showed largely decreased current, and the blend device showed dramatically increased current. The changed in the current of both samples was found to be maintained and stable for at least that length of time.

Figure 7:
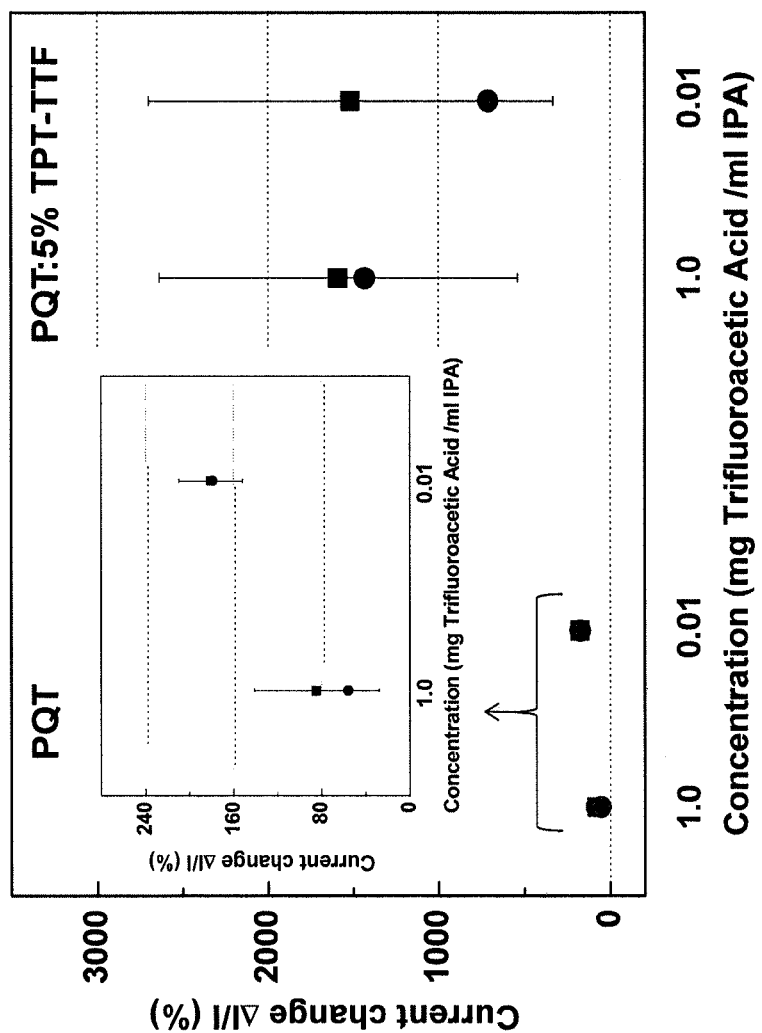
FIG. 7 shows output curve current change $\Delta I/I$ (%) at $V_D=V_G=-40$ V of pure PQT12 device (inset: expanded part) and blended PQT12:5% TPT-TTF device after dropping 15 µl of 1.0 and 0.01 mg trifluoroacetic acid/ml IPA solution on 0.81 cm² area. Circle and square show median and mean value, respectively. The bar shows standard deviation.

We also investigated the effect of exposure of trifluoroacetic acid (TA) to PQT12 and PQT12:5% TPT-TTF blend devices (FIG. 7), as a representative acidic interferent that we would expect to act as a dopant. In contrast to TNT exposure of a pure PQT12 OFET, the current of the OFET when exposed to 1.0 and 0.01 mg TA/ml IPA did indeed increase. In addition, after exposure to the same TA solutions, the PQT12: 5% TPT-TTF blend device showed even greater increased relative current. Thus, the combination of responses of pure and TPT-TTF-blend OSCs to acid and to TNT is different.

Figures 8A, 8B:
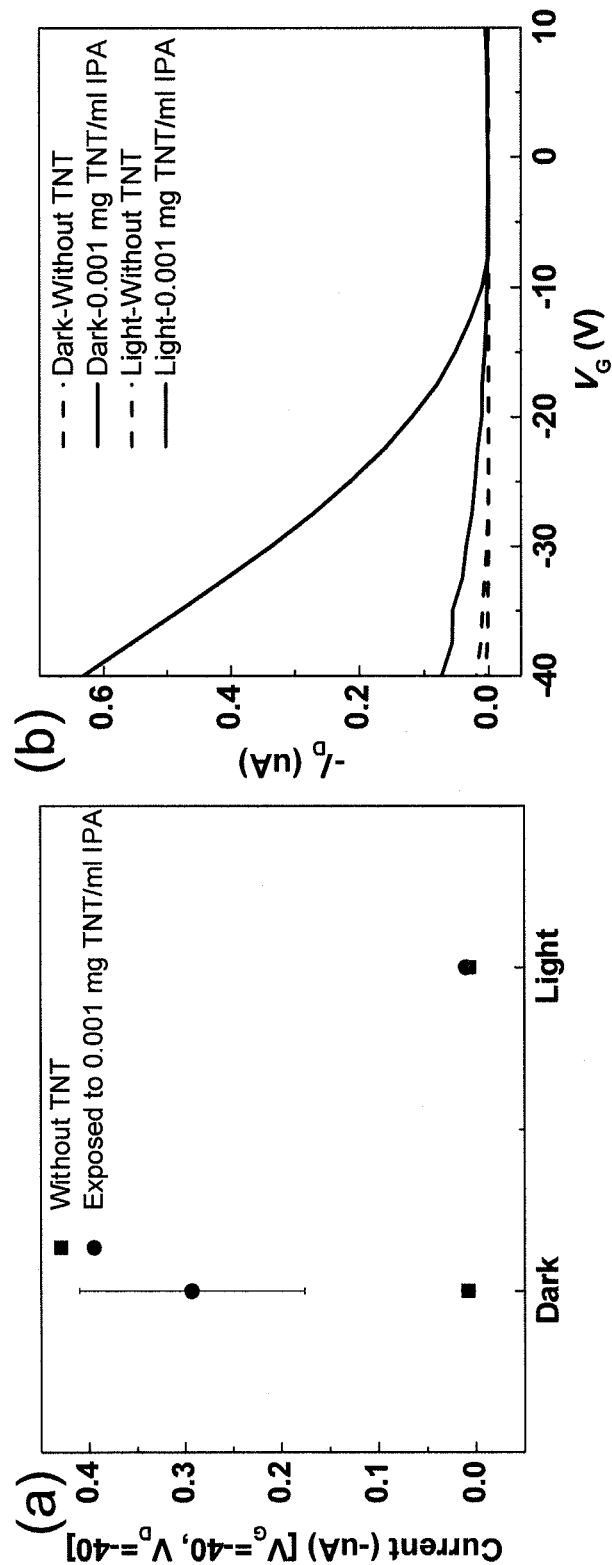
FIG. 8A shows output curve current change at $V_D=V_G=-40$ V and FIG. 8B transfer curve of PQT12:5% TPT-TTF device before and after dropping 15 µl of 1.0 and 0.001 mg TNT/ml IPA solution on 0.81 cm² area, in dark and bright condition.

Finally, we checked the responses under dark and brightly lit conditions (FIGS. 8A-8B). Under dark conditions, the hole current of the PQT12:5% TPT-TTF blend device exposed to 10$^{-3}$ mg TNT/ml IPA was much more augmented than under bright conditions.

Conclusion

In summary, we showed the increased current "turn-on" response using PQT12:TPT-TTF blend OFETs when exposed to very dilute TNT analyte solution in contrast to many of the OFETs exposed to various chemical compounds. The PQT12:10% TPT-TTF blend device exposed to 190 pg TNT/cm$^2$ showed 3000% increased current which is the best response to TNT explosive so far.

References for Example 1

(1) See, K. C.; Becknell, A.; Miragliotta, J.; Katz, H. E. *Adv Mater* 2007, 19, 3322.

(2) Torsi, L.; Tanese, M. C.; Cioffi, N.; Gallazzi, M. C.; Sabbatini, L.; Zambonin, P. G.; Raos, G.; Meille, S. V.; Giangregorio, M. M. *J Phys Chem B* 2003, 107, 7589.

(3) Huang, J.; Miragliotta, J.; Becknell, A.; Katz, H. E. *J Am Chem Soc* 2007, 129, 9366.

(4) Huang, J.; Sun, J.; Katz, H. E. *Adv Mater* 2008, 20, 2567.

(5) Huang, J.; Dawidczyk, T. J.; Jung, B. J.; Sun, J.; Mason, A. F.; Katz, H. E. *J Mater Chem* 2010, 20, 2644.

(6) Royer, J. E.; Lee, S.; Chen, C.; Aim, B.; Trogler, W. C.; Kanicki, J.; Kummel, A. C. *Sensor Actuat B-Chem* 2011, 158, 333.

(7) Zhu, Z. T.; Mason, J. T.; Dieckmann, R.; Malliaras, G. G. *Appl Phys Lett* 2002, 81, 4643.

(8) Li, D. W.; Borkent, E. J.; Nortrup, R.; Moon, H.; Katz, H.; Bao, Z. N. *Appl Phys Lett* 2005, 86.

(9) Crone, B.; Dodabalapur, A.; Gelperin, A.; Torsi, L.; Katz, H. E.; Lovinger, A. J.; Bao, Z. *Appl Phys Lett* 2001, 78, 2229.

(10) Chang, J. B.; Liu, V.; Subramanian, V.; Sivula, K.; Luscombe, C.; Murphy, A.; Liu, J. S.; Frechet, J. M. J. *J. Appl. Phys.* 2006, 100.

(11) Torsi, L.; Marinelli, F.; Angione, M. D.; Dell'Aquila, A.; Cioffi, N.; De Giglio, E.; Sabbatini, L. *Org Electron* 2009, 10, 233.

(12) Tremblay, N. J.; Jung, B. J.; Breysse, P.; Katz, H. E. *Advanced Functional Materials* 2011.

(13) Ong, B. S.; Wu, Y. L.; Liu, P.; Gardner, S. *J Am Chem Soc* 2004, 126, 3378.

EXAMPLE 2

In this example, we provide a synthesis route to a thiophene polymer where the repeat unit consists of 3,3'''-didodecylquaterthiophene (as in PQT12) plus an additional thiophene ring from which other functional groups may be projected. The hydroxymethyl form of this polymer, while only a poor semiconductor in its own right, serves as a vehicle for compatibilizing PQT12 itself with arbitrary functional groups. In this manuscript, we focus on tetrathiafulvalene (TTF) as the functionality. As expected, the TTF group acts as a hole trap, but this enables a current-increase response to trinitrotoluene as an analyte, and confirms a similar observation we recently reported for a dissolved TTF.

Solution-processable organic and polymeric semiconductors are being considered for low-cost electronic devices due to their modulated electronic conductivity combined with other functionality.)[1-4] Applications include light-emitting diodes (OLEDs),[5,6] organic field effect transistors (OFETs),[7,8] organic photovoltaic cells (OPV),[9,10] chemical sensors,[11] and thermoelectrics[12]. Polythiophenes are frequently used as processable semiconducting polymers. Their substitution chemistry allows attachment of functional groups for activity beyond simple electronic switching. For example, side-chain functionalization of polythiophenes has been reported to influence the optical and electronic properties due to the interaction of the polymer backbone with the functional group,[13-16] Oligothiophenes with thiol,[17,18] bisulfide,[19] thioacetate,[20] and thiocyanate[21] terminated functionality have been reported to show a rapid self-assembling behavior. Furthermore, polymer aggregation in form of hollow spheres, lamella, and hollow cylinders have been observed from the self-organization of rod-coil polymers based on hole-transporting unit (carbazole) or electron transporting unit (fluorene/thiophene) on the side chain.[22-25] Alkyl ether,[26-29] crown-ether,[30] calixarene,[31] and porphyrin[32] functionalized polythiophenes have been widely investigated for the recognition of metal cations. Also, postfunctionalization has been demonstrated on polythiophene wherein the substitution with phenyl, p-tolyl, 2- and 4-methoxyphenyl, biphenyl, 1-naphthyl, 2-thienyl, and phenylethylenyl groups caused red shifts in the absorption and emission.[33]

In this example, we consider the tetrathiafulvalene (TTF) group as a side chain. As discussed above, we had already discovered that TTF mixed as a small molecule with a polythiophene in a sensor element displayed a unique spectrum of responses to trinitrotoluene (TNT) exposures, including many cases of induced current increases.[34] This is contrary to what is typically observed from chemical interactions with organic semiconductor devices, where currents decrease.[35-40] Having both response signs available allows fabrication of more specific, binary, and ratiometric sensing circuits.[41]

The first reported example of a poly(thiophene)-TTF was an electropolymerized product reported by Bryce and coworkers.[66] Roncali and coworker synthesized the monomer 3-(10-tetrathiafulvalenyl-9-oxadec-1-yl)thiophene and electropolymerized it successfully in nitrobenzene.[67] Further, the group electropolymerized TTF-derivatized polythiophene based on bithiophene or ethylenedioxythiophene (EDOT), resulting in an extensively π-conjugated TTF-derivatized polythiophene. The group investigated the behavior of TTF in the polymeric backbone, wherein they reported the presence of different monomeric and dimeric oxidized TTF species.[68,69] PEDOT with side chain functionality of ω-iodo-alkyl and co-iodo-polyether has been synthesized by electropolymerization of respective monomer and was subjected to postfunctionalization with a functional block bearing a thiolate derivative of TTF.[70] The desired polymer was substituted with two polyether chains and was shown that the binding of $Pb^{2+}$ could be driven electrochemically.[71]

Our synthetic approach begins with a hydroxymethyl-substituted copolymer, which was then substituted with TTF-derivatized monomer as side chain functionality. This TTF-side chain polymer was active for TNT detection in a manner similar to what we had observed for the small molecule.[34] This demonstrates the new polymer as a vehicle for compatibilizing the often-insoluble TTF with an electron-rich polymer, and also shows that the response we reported previously was not due to a special solid state effect of the small molecule.

Synthesis of Monomers and Polymers. The syntheses of the initial hydroxymethyl polymer and O-alkyl derivatives are outlined in Schemes 1 and 2, respectively. The synthesis of the monomer 3,3'''-Didodecylquaterthiophene was obtained as reported in the literature in 75% yield by Stille coupling of two equivalents of 2-bromododecylthiophene with 5,5'-bis(trimethyltin)-2,2'-bithiophene.[72] 2,2'-Dibromo-3-3'''-didodecyl-quaterthiophene was then subjected to bromination using two equivalents of n-bromosuccinimide (NBS) in chloroform/acetic acid. The product was confirmed by the appearance of a singlet peak at 6.89 ppm in $^1$H NMR corresponding to the C—H proton at the 2-position of the thiophene ring. Thiophen-3-ylmethyl acetate was synthesized from thiophen-3-ylmethanol, which when subjected to acetylation using acetyl chloride in presence of DMAP as a catalyst resulted in the desired compound in good yield.[73] Thien-3-ylmethanol was obtained from the reduction of thiophene-3-carboxaldehyde using $LiAlH_4$. $^1$H NMR confirmed the product. A functionalized TTF derivative was synthesized by subjecting TTF to monolithiation using lithium diisoproplyamide as reported in the literature. The monolithiated product hence formed was formylated using N-methyl-N-phenylformamide, which then upon reduction with $NaBH_4$ in methanol resulted in 4-formyltetrathiafulvalene.[74] 4-Formyltetrathiafulvalene was then substituted with 1,8-dibromooctane in a THF/DMF solvent mixture, which resulted in 4-(((8-bromooctyl)oxy)methyl)-2,2'-bi(1,3-dithiolylidene) in 65% yield. The product was confirmed by the disappearance of the —OH peak at 1.9 ppm and the appearance of two different types of triplet at 3.40 ppm and 3.42 ppm.

Scheme 1. Synthesis of TTF based side chain unit

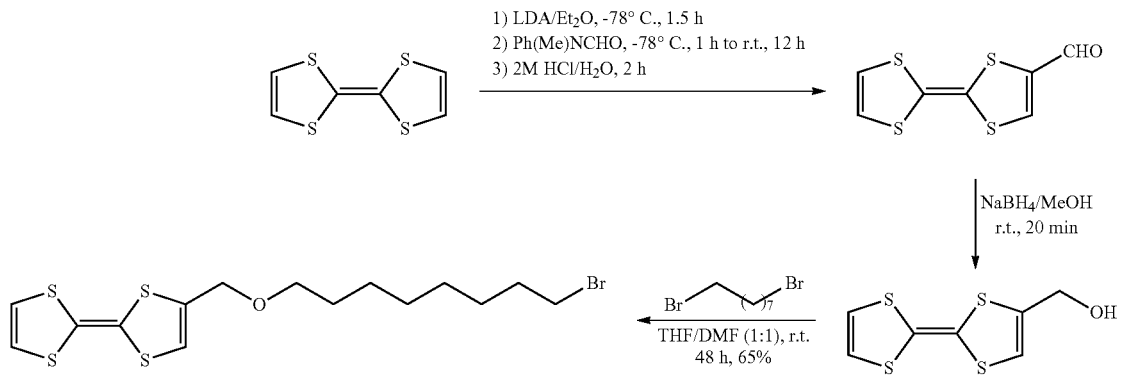

The above mentioned monomers were then used for the synthesis of copolymers. An alternating copolymer containing 3,3'''-Didodecylquaterthiophene and Thiophen-3-ylmethyl acetate were polymerized via direct arylation. The polycondensation reaction of a 1:1 ratio of the two monomers was carried out at 100° C. in the presence of Pd(OAc)$_2$ as a catalyst with pivalic acid and K$_2$CO$_3$ in dimethylacetamide.[75]

methanol, which resulted in polymers in good yield. The copolymers P1-P3 were found to be highly soluble in chloroform, chlorobenzene, methylene chloride, THF and toluene. The equimolar ratio of the monomer in the copolymer was confirmed by $^1$H NMR wherein the CH$_2$ proton of methylene group and the CH$_2$ of alkyl chain integration ratio corresponded to 1:1. In addition, the disappearance of the OH Scheme 2. Synthesis of Hydroxymethyl Copolymer P1.

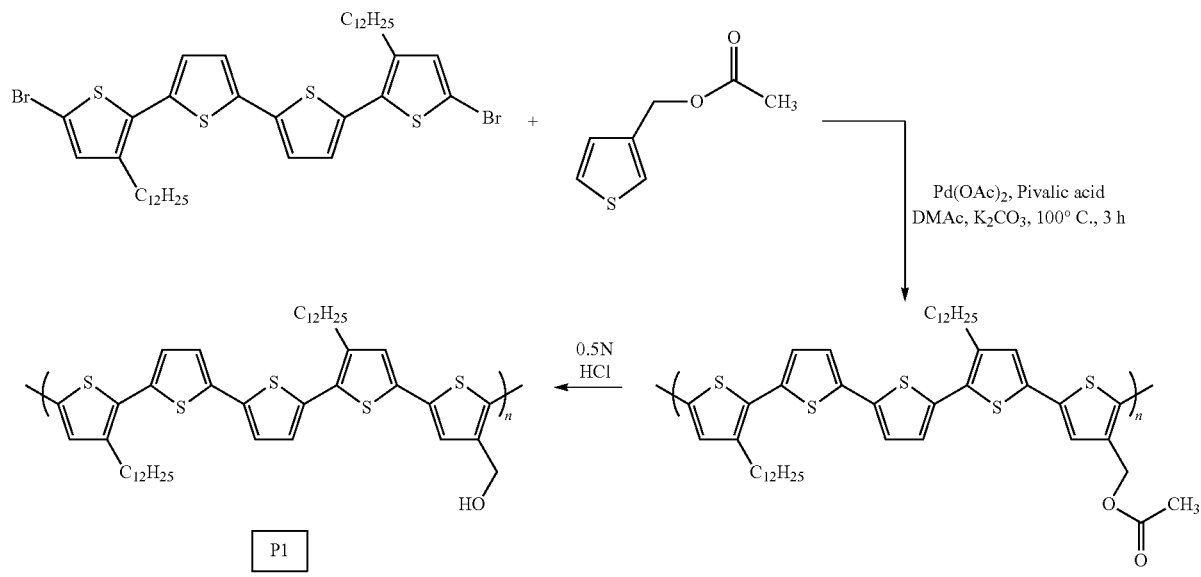

The copolymer hence obtained was then subjected to the deprotection of the acetyl group by treating it with 0.5 N HCl, resulting in —OH functionalized copolymer (P1). The copolymer was then subjected to O-alkylation with 4-(((8-bromooctyl)oxy)methyl)-2,2'-bi(1,3-dithiolylidene) or propargyl bromide in presence of NaH in THF with DBU as the catalyst, resulting in copolymer with TTF derivative (P2) and propargyl side chains (P3) (Scheme 3). Polymers were isolated by extracting from chloroform. The concentrated chloroform solution was added dropwise to methanol, where red precipitation was observed. The red precipitate was subjected to soxhlet extraction using methanol, hexane and finally with chloroform. The chloroform layer was reprecipitated thrice in peak at 2.1 ppm confirmed the desired polymer. The appearance of a broad peak at 4.2 ppm and 3.5 ppm corresponding to methylene protons of TTF and OCH$_2$ respectively for the copolymer with TTF as the side chain functionality confirmed the desired copolymer, whereas the appearance of a peak at 2.5 ppm corresponding to acetylene proton confirmed the acetylenic functionalized copolymer. While not essential to the present study, the acetylenyl group provides a route to further derivitization via "click" cycloaddition chemistry with azides. GPC studies indicated a weight average molecular weight of 10 KDa (PDI 2.89) for P1, 11 KDa (PDI 2.2) for P2, and 12 KDa (PDI 2.41) for P3.

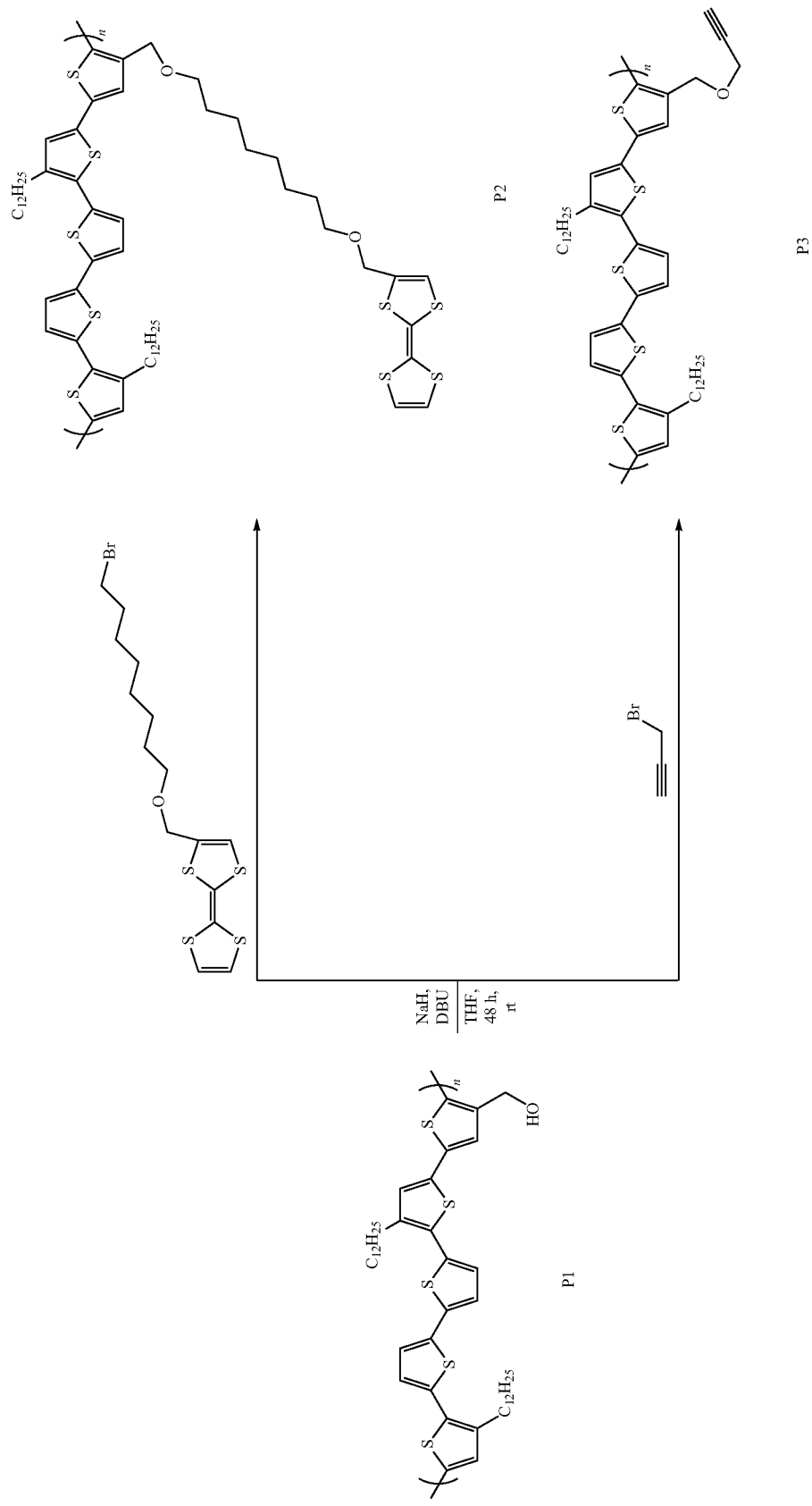

Thermal Analysis

Figure 9:
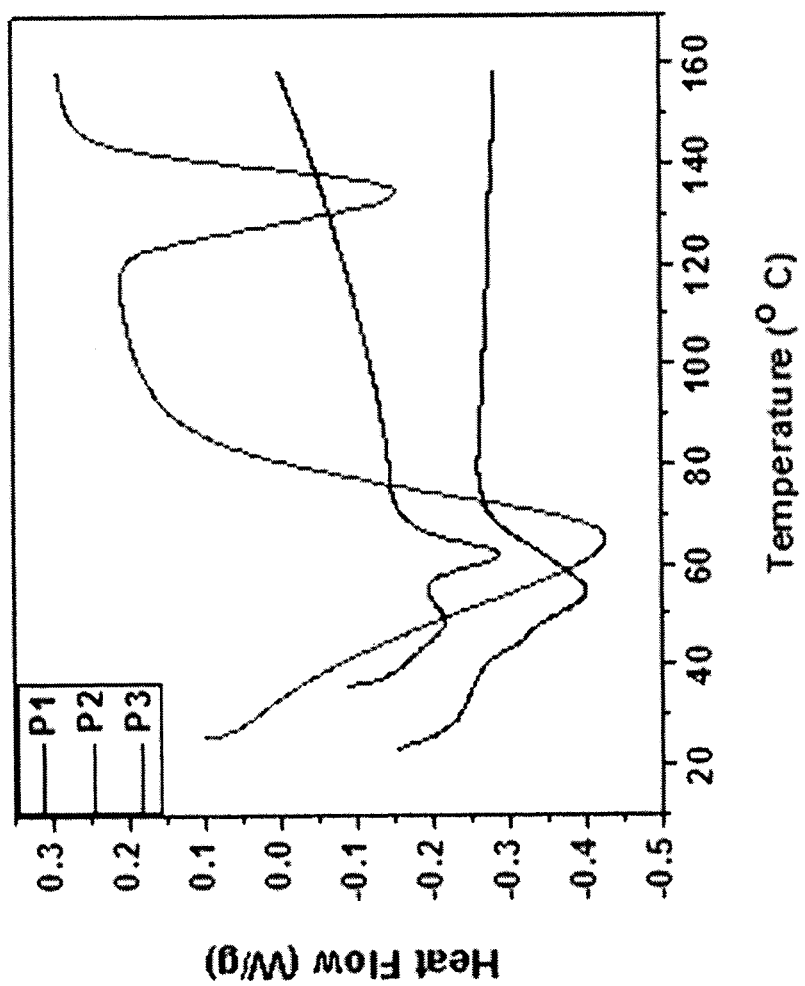
FIG. 9 shows DSC thermogram of P1-P3 with heating rate of 5° C./min under an inert atmosphere.

FIG. 9 shows the thermal equilibration behavior of P1, P2 and P3 investigated with differential scanning calorimetry (DSC). The samples were dried at room temperature under high vacuum before testing.

Features were observed for copolymers P1, P2, and P3 at 54.4° C., 65.2° C. and, 61.9° C. respectively on initial heating. In addition, P2 showed a second peak at 134.5° C. These transitions may reflect loss of the last traces of solvent, or conformational stabilization. The peaks are not observed on cooling or reheating, as was also the case for poly(3-hexylthienylene vinylene).[76]

Optical Properties of the Polymers

Figure 10:
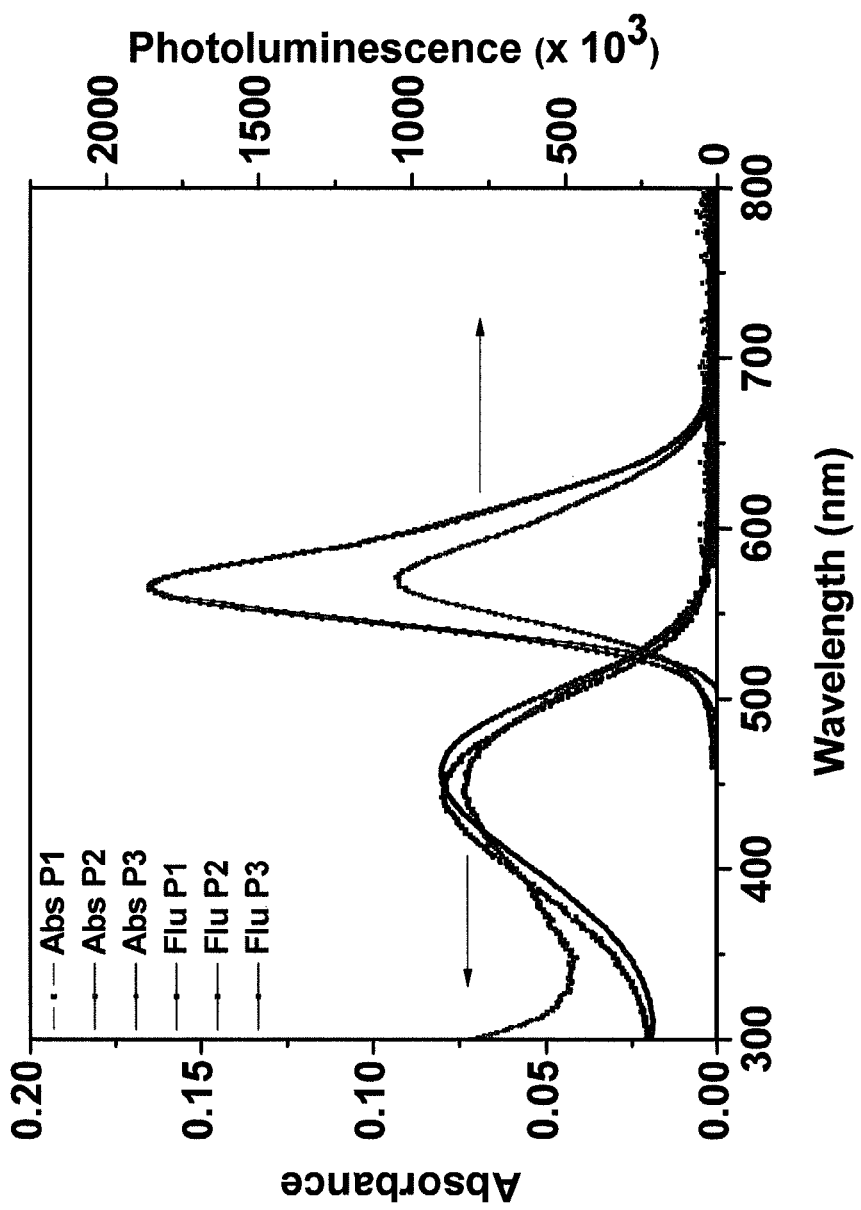
FIG. 10 shows absorption and emission spectra of the polymers in chloroform.

FIG. 10 shows the absorption and emission spectra of the polymer solutions in chloroform. The absorption spectra of P1-P3 showed an absorption maximum at 446 nm, 449 nm, and 456 nm respectively that is typical of the π-π* transition in chloroform. Emission maxima of P1-P3 were observed at 565 nm, 570 nm and 565 nm respectively in chloroform. The side substituents seem to have little effect on the emission wavelengths of the polythiophene backbone. However, the fluorescence intensity was observed to decrease by a factor of 2 with the substitution of the TTF group into the side chains, showing possible electron transfer quenching activity by the TTF. Data are listed in Table 1.

TABLE 1

Absorption and Emission Spectral Properties

| Polymers | $\lambda^{abs}_{max}$ (nm) | $\lambda^{flu}_{max}$ (nm) | $E_g^{opt}$ (eV)[a] |
|---|---|---|---|
| P1 | 446 | 565 | 2.21 |
| P2 | 449 | 570 | 2.23 |
| P3 | 456 | 565 | 2.23 |

[a]Optical band gap was obtained from empirical formula, $E_g^{opt} = 1241/\lambda_{edge}$, where $\lambda_{edge}$ is the onset wavelength of its absorption peak in the longer wavelength direction.

Figure 17:
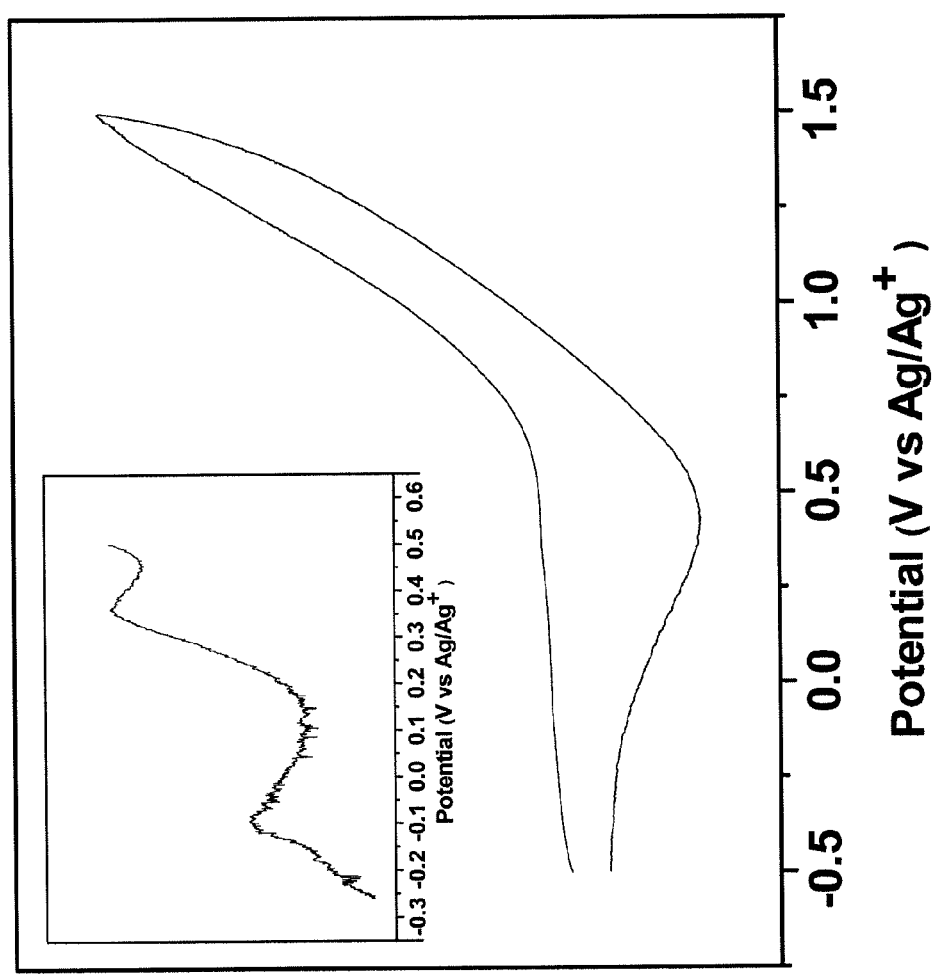
FIG. 17 Above-cyclic voltammograms recorded as thin films on Pt electrodes in 0.1 M TBAP/CH$_3$CN with a scan rate of 100 mV/s. Below, cyclic voltammogram of P2 recorded in solution (CH$_2$Cl$_2$ as the solvent). The inset is an expansion of the interval between −0.3 and 0.6 V. The reference is Ag/Ag$^+$. The peak at −0.09 V may have been from a TTF aggregate.
Figure 18:
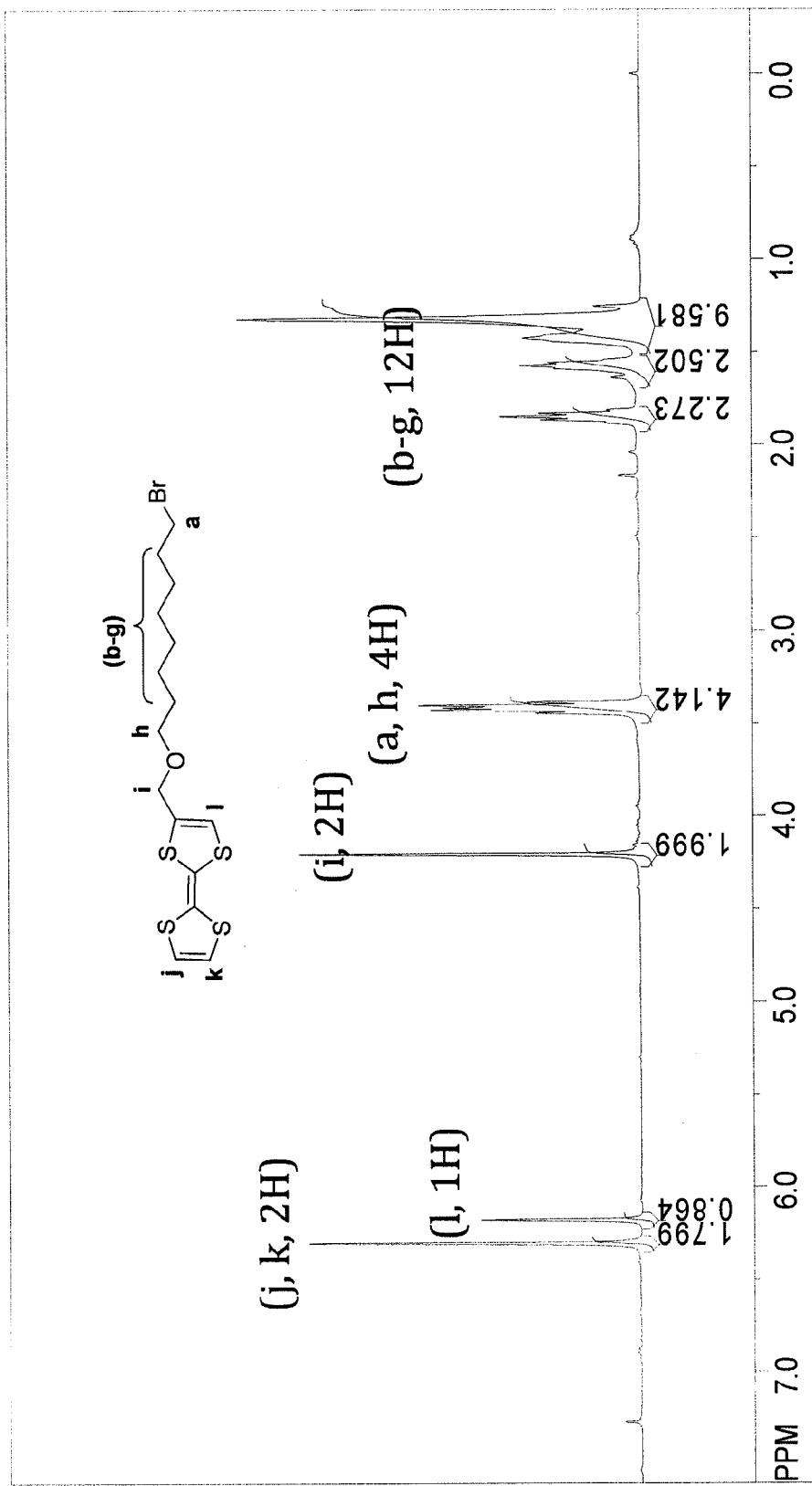
FIG. 18 provides data for $^1$H NMR of monomer based on TTF derivative.
Figure 19:
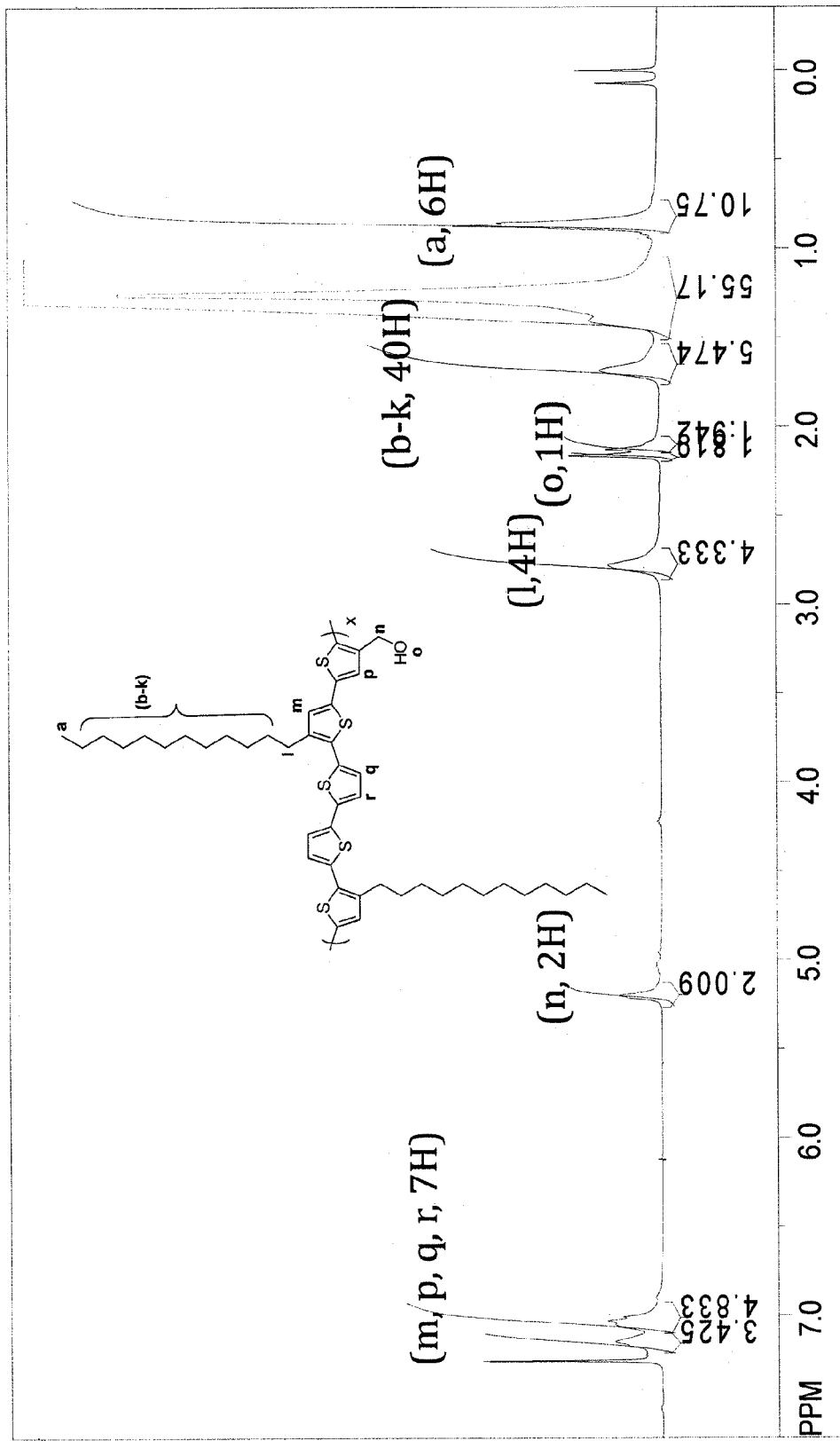
FIG. 19 provides data for $^1$H NMR of P1.
Figure 20:
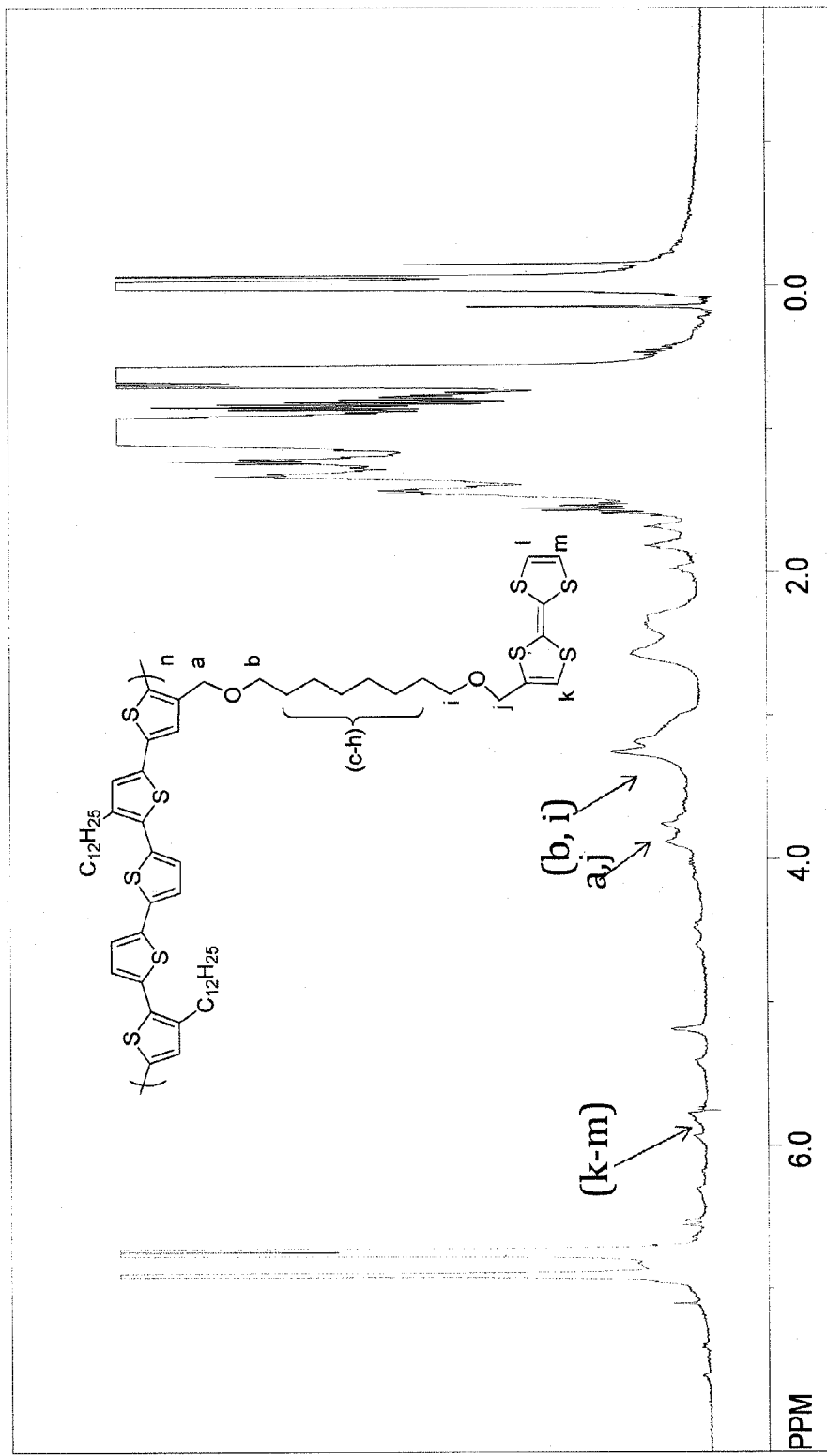
FIG. 20 provides data for $^1$H NMR of P2.
Figure 21:
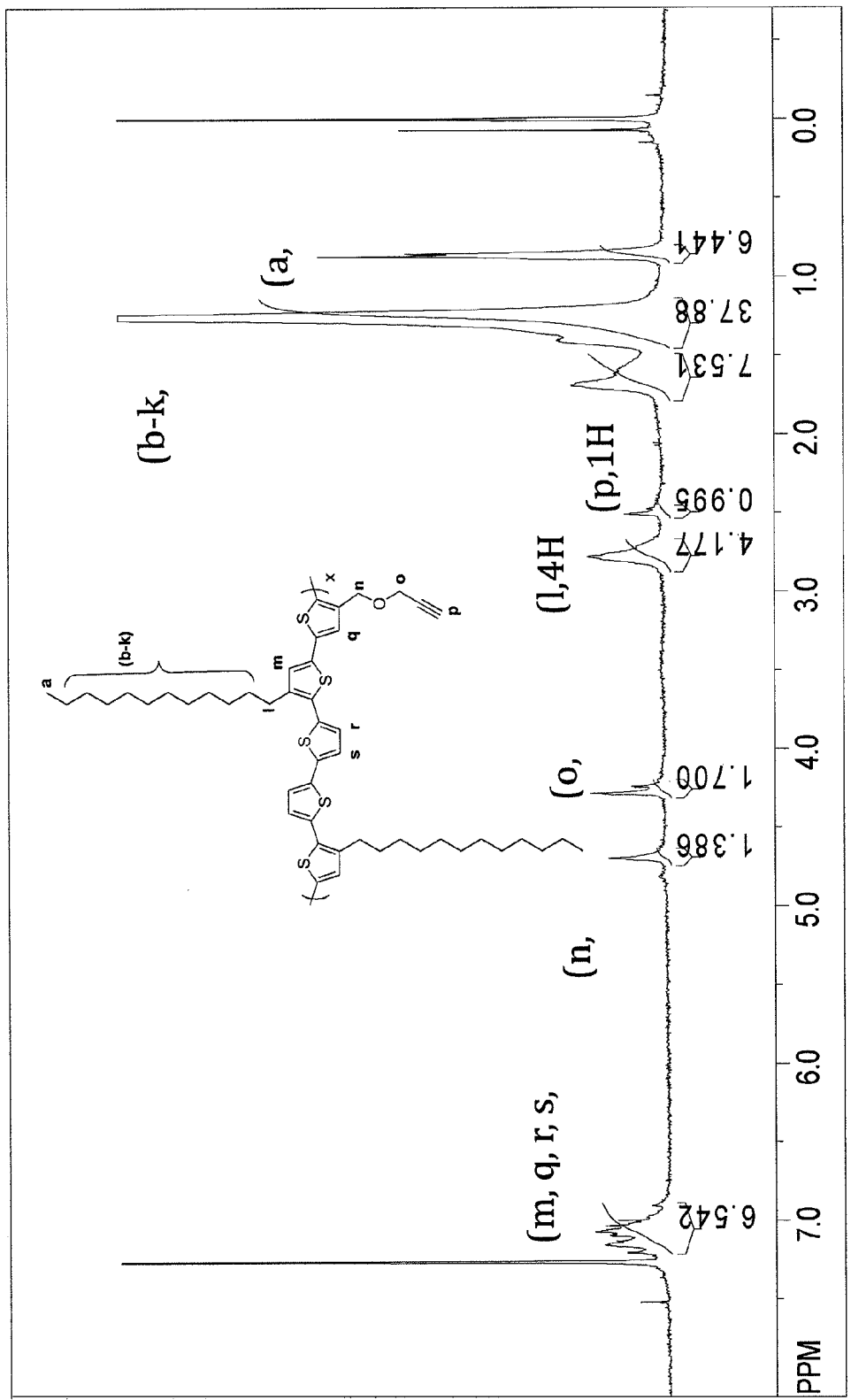
FIG. 21 provides data for NMR of P3.

Electrochemical Properties. FIG. 17 shows the cyclic voltammograms of the polymer films on the Pt electrode by scanning the potential from −2.0 V to 1.8 V vs Ag/Ag$^+$ at the scan rate of 100 mV/s. Platinum wire was used as the working electrode, solution cast P1-P3 on a Pt button electrode was used as the counter electrode, Ag/Ag$^+$ (0.01 M AgNO$_3$) was used as the reference electrode, and 0.1 M TBAP in acetonitrile was used as the supporting electrolyte. While a separate TTF oxidation peak was not apparent in the cyclic voltammogram of the P2 film, the peak was discernible near 0.36 V in a solution-phase cyclic voltammogram using the same supporting electrolyte and reference electrode, shown as the lower chart in FIG. 17. Data are listed in Table 2.

TABLE 2

Electrochemical Onset Potential and band gap of the Polymer Films

| Polymers | $\phi_{ox}$ (V vs Ag/Ag$^+$)/$E_{HOMO}$ (eV) | $\phi_{ox}$ (V vs Ag/Ag$^+$)/$E_{LUMO}$ (eV) | $E_g^{ec}$ (eV)[a] |
|---|---|---|---|
| P1 | 0.69/−5.39 | −1.39/−3.31 | 2.08 |
| P2 | 0.80/−5.50 | −1.32/−3.38 | 2.12 |
| P3 | 0.44/−5.14 | −1.42/−3.28 | 1.86 |

[a]HOMO and LUMO levels are calculated from the onset of the first peak of the corresponding redox wave and are referenced to ferrocene, which has a HOMO of −4.8 eV.

Field-Effect Transistor Properties of the Polymers. OFETs with P1 showed a typical p-channel behavior, but with low mobility of up to $1.4 \times 10^{-5}$ cm$^2$/Vs and an on/off ratio of $10^3$, whereas P2 and P3 did not show any OFET behavior. The P1 was less ordered than the parent PQT12 polymer, as shown by x-ray diffraction indicating amorphous structure. For P2, the lack of OFET activity was expected, as the TTF group should act as a powerful hole trapping site.[34] The propargyl group might be reactive in the presence of holes, or may disrupt the morphology even more than the hydroxymethyl group because of unproductive π-interactions.

Figure 11A:
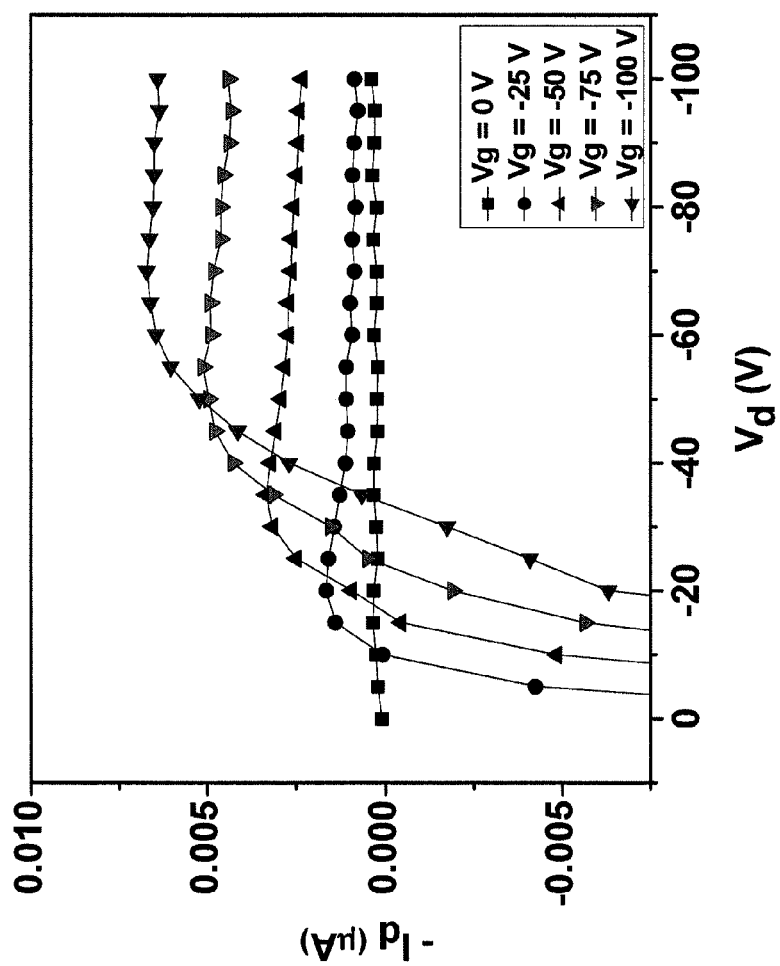
FIG. 11A shows OFET response plot for P1 measured under ambient condition.
Figure 11B:
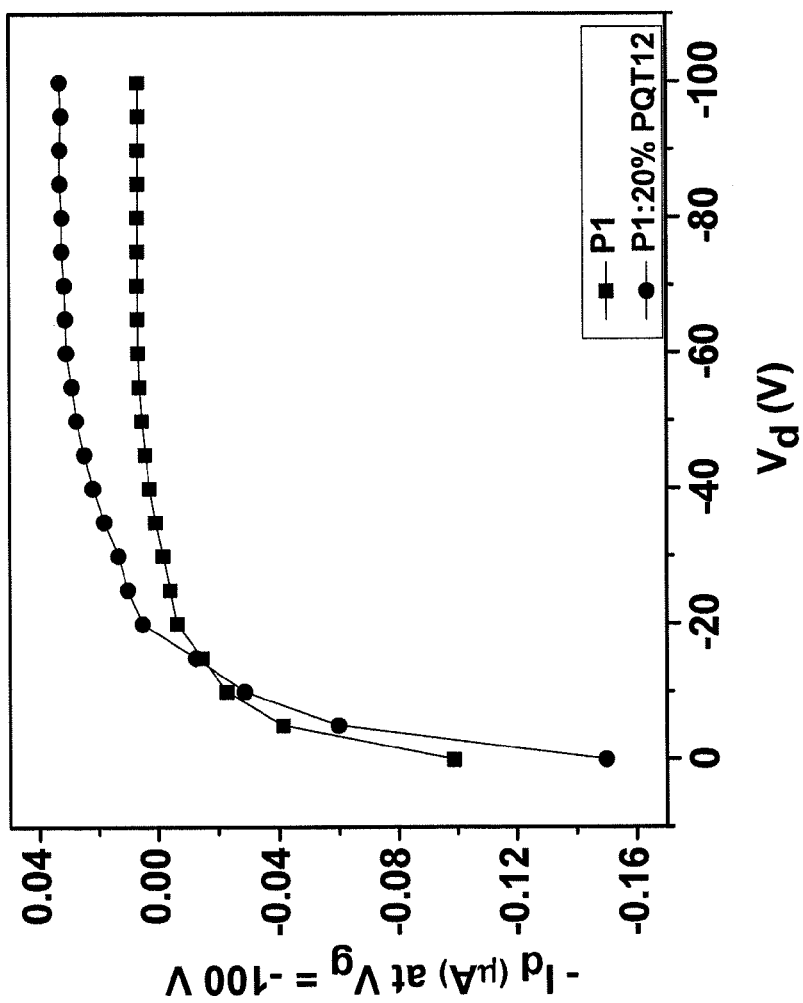
FIG. 11B Comparison of output curve at $V_g=-100$ V for P1 and P1 blended with 20 wt % PQT12.
Figure 11C:
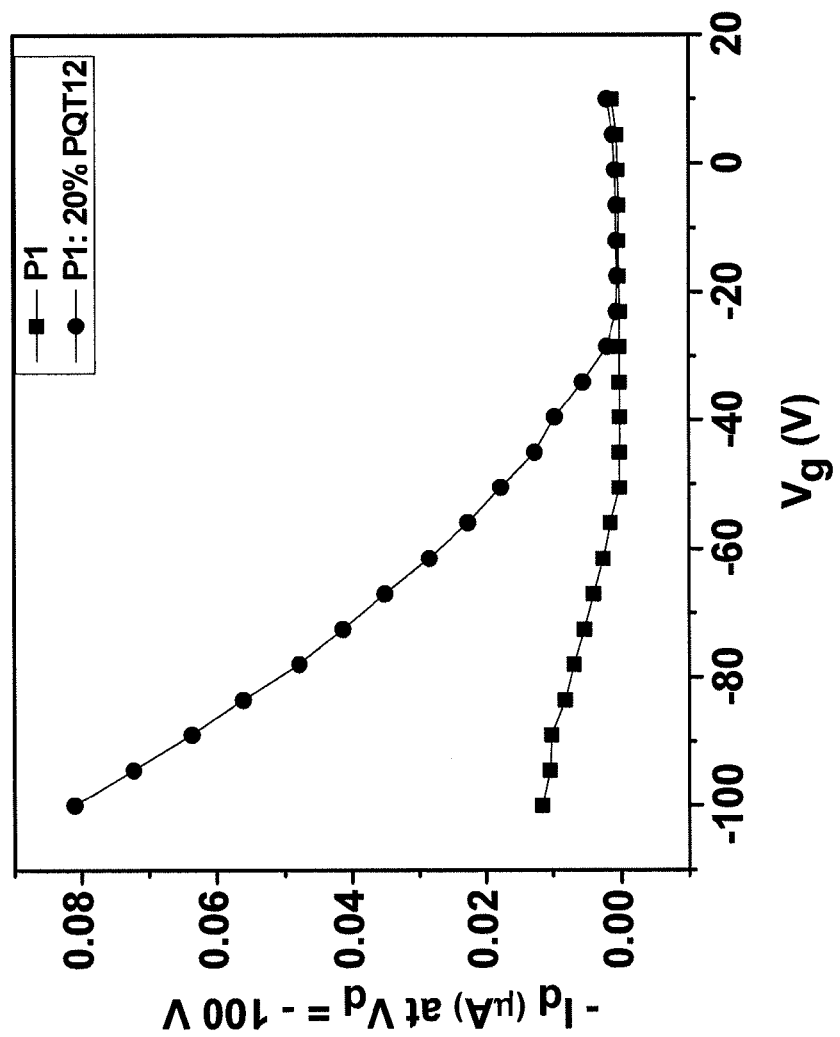
FIG. 11C Comparison of transfer curve at $V_d=-100$ V for P1 and P1 blended with 20 wt % PQT12.

When P1 was blended with just 20 wt % PQT12, the OFET performance significantly improved. The drain current was observed to increase 8 times at Vg=−100 V, with mobility of $5.1 \times 10^{-5}$ cm$^2$/Vs and on/off ratio of $10^2$. FIGS. 11A-11C show the typical output and transfer curves of OFET device with P1 and its blend with PQT12. This shows that P1 can be a compatible additive for introducing OH groups into active PQT12 films.

Figure 12A:
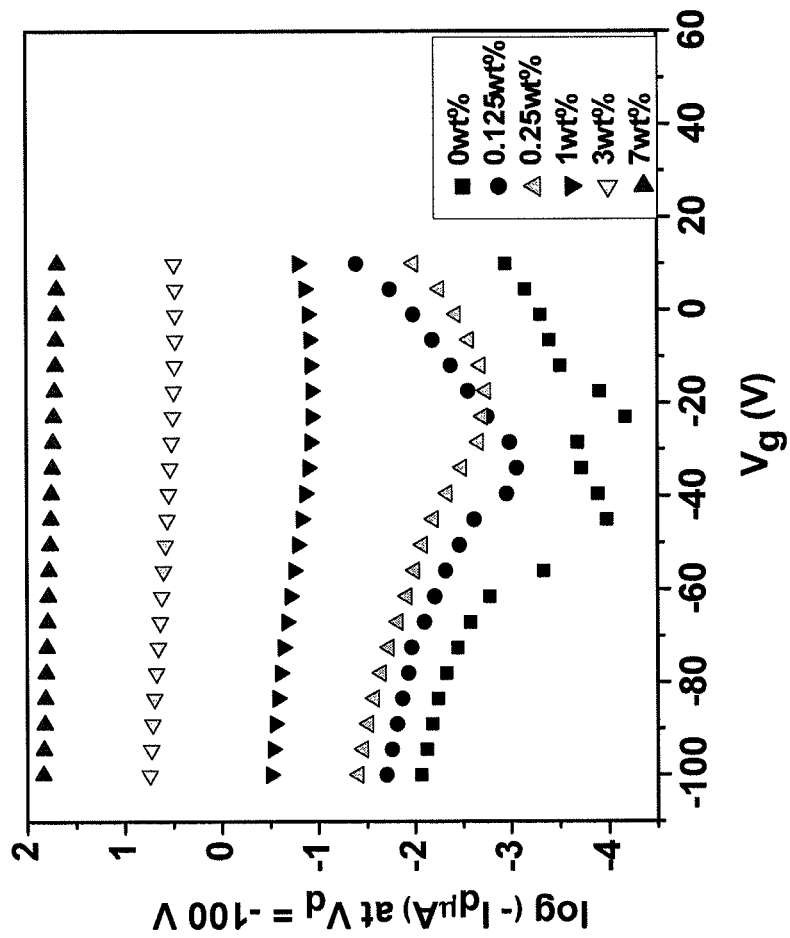
FIG. 12A provides logarithmic transfer curve of P1 doped with different wt % of F4TCNQ at $V_d=-100$ V.
Figure 12B:
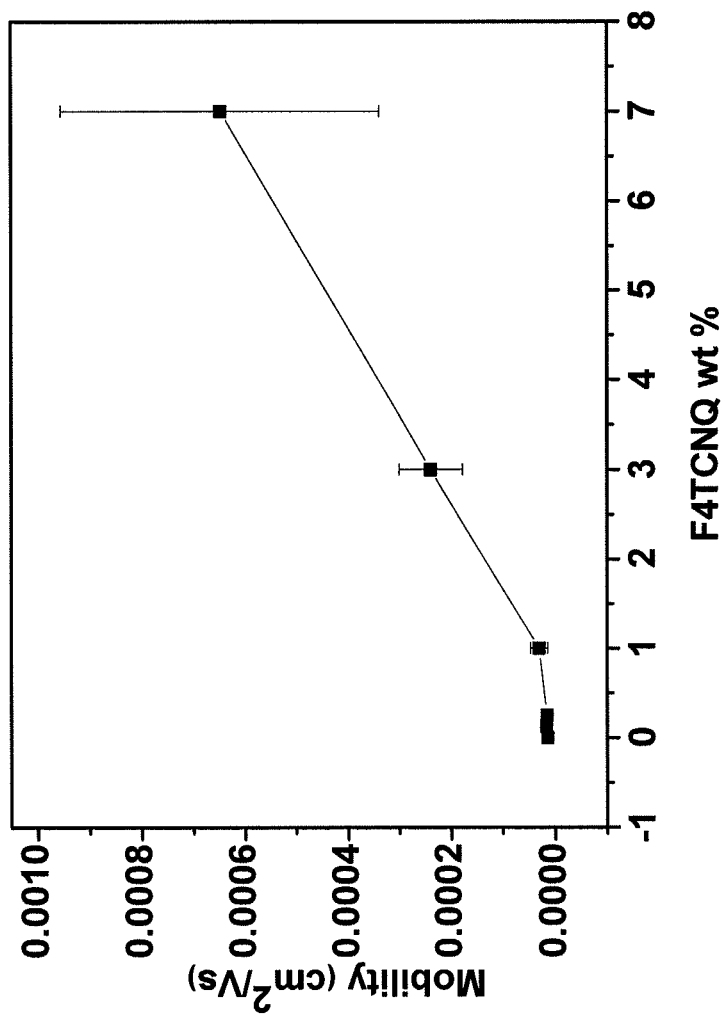
FIG. 12B Change in mobility of P1 with the increase in the dopant concentration. When the wt % of F4TCNQ dopant was increased to 3% and 7%, respectively, a further increase in current was observed and mobility increasing by an order of magnitude. F4TCNQ did not confer OFET behavior on P2 or P3.

OFET Properties of the Polymers with F4TCNQ as the Dopant. Tetrafluorotetracyanoquinodimethane (F4TCNQ), an electron acceptor, is an effective p-type dopant to increase polythiophene. conductivity.[77] We made doped films by spin-coating different ratios of 10 mg/mL of P1-P3 with 0.5 mg/mL of F4TCNQ in chlorobenzene solution under ambient conditions at 1500 rpm. for 60 sec, followed by storage in a vacuum dessicator for 30 min prior to measurement. We investigated doping of P1 with 0.125 wt %, 0.25 wt %, 1.0 wt %, 3 wt % and 7 wt % of F4TCNQ by checking the output and transfer characteristics of bottom contact OFETs. Normal p-type OFET behavior was observed with 0.125 wt % and 0.25 wt % F4TCNQ, with slight increase in the current. When P1 was doped with 1.0 wt % of F4TCNQ, the current significantly increased by 2 orders of magnitude, but was only slightly adjusted by the gate voltage, indicating continued low mobility. The device was "ON" at zero applied gate voltage, with drain current of 2.6 μA (FIGS. 12A-12B and Table 3).

TABLE 3

Dopants and properties for P1 deposited from 10 mg/mL solution

| F4TCNQ (wt %) | μ (cm$^2$/Vs) ± Std dev | $I_{on}/I_{off}$ |
|---|---|---|
| 0 | $1.4 \times 10^{-5} \pm 3.1 \times 10^{-6}$ | $2 \times 10^3$ |
| 0.125 | $1.6 \times 10^{-5} \pm 4.7 \times 10^{-6}$ | 22 |
| 0.25 | $1.6 \times 10^{-5} \pm 5.3 \times 10^{-6}$ | 20 |
| 1.0 | $3.1 \times 10^{-5} \pm 1.6 \times 10^{-5}$ | 2.6 |
| 3.0 | $2.4 \times 10^{-4} \pm 6.1 \times 10^{-5}$ | 1.8 |
| 7.0 | $6.5 \times 10^{-4} \pm 3.1 \times 10^{-4}$ | 1.4 |

Figure 13A:
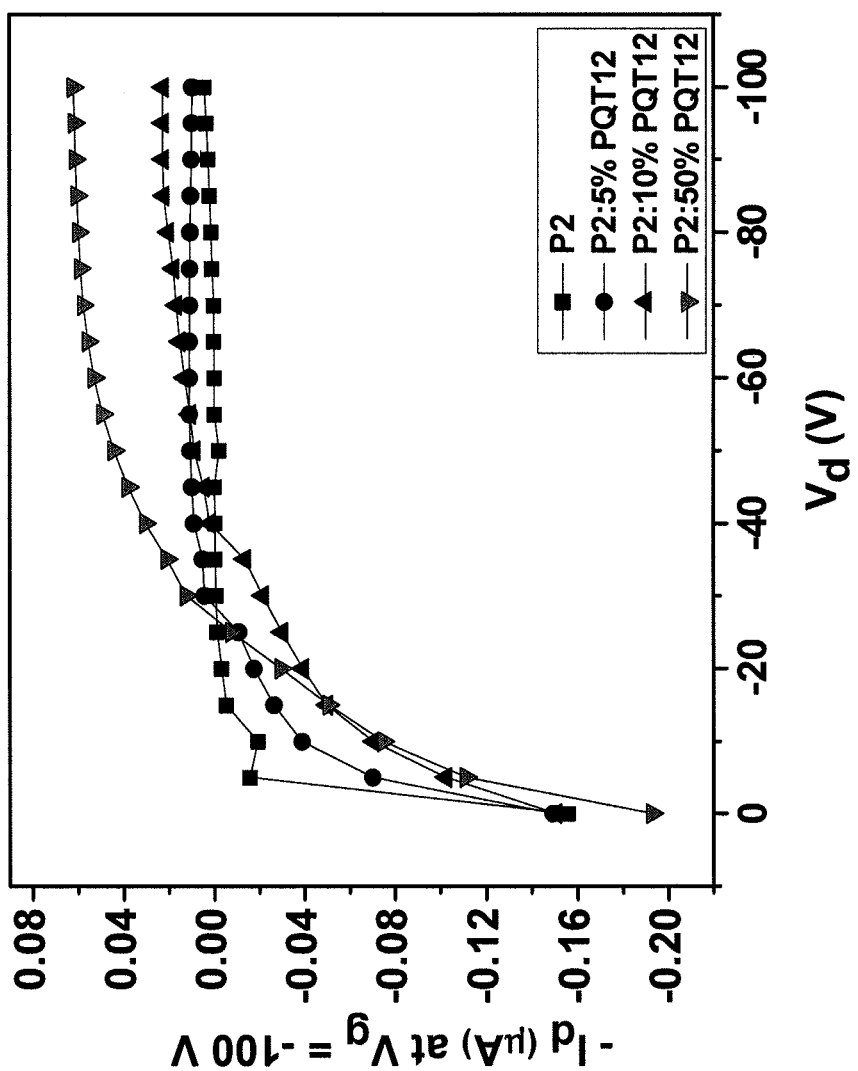
FIG. 13A provides a comparison of output curve at $V_g=-100$ V for different blend ratio of P2:PQT12 measured under ambient condition.
Figure 13B:
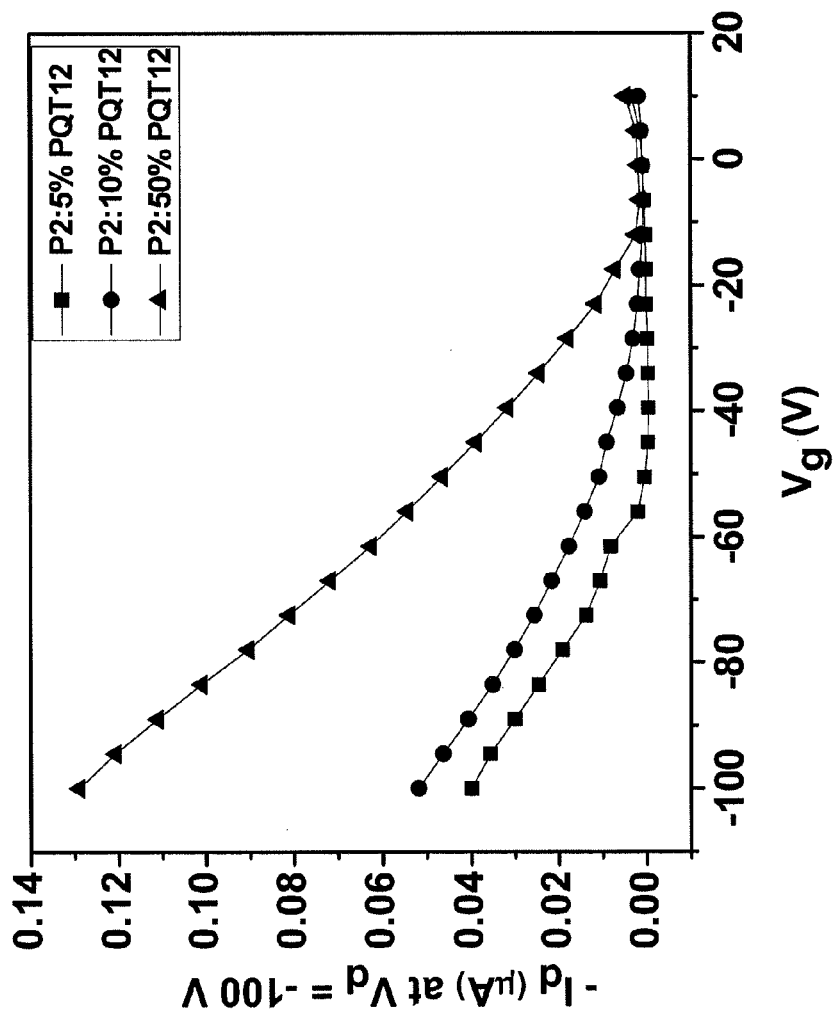
FIG. 13B Comparison of Transfer curve at $V_d=-100$ V for different blend ratio of P2:PQT12 measured under ambient condition.

TNT Sensing of P2. As discussed above, PQT12 blended with tetrakis(pentylthio)TTF (TPT-TTF) in an OFET geometry and not showing OFET behavior, when exposed to dilute TNT analyte solution, resulted in "turn-on" response of the current, which we attribute to complexation between TPT-TTF and TNT. Pure P2, and P2 with 5 or 10% PQT12 added, showed negligible OFET activity. However, a 50-50 wt % blend of P2 and PQT12, as shown in FIGS. 13A-13B. All the blend devices were then exposed to ≥$10^{-4}$ mg TNT/mL in 2-propanol (IPA). The TNT solution was dropped on 0.81 cm$^2$ of Novec fluoropolymer-bounded channel area with several OFET channels. When pure IPA solvent was dropped and dried on various blend ratio of P2:PQT12 films, no significant current changes were observed. The pure P2 devices when exposed to ≥$10^{-4}$ mg TNT/mL in 2-propanol (IPA) did not show any transistor behavior. The blended P2 with 5 wt % PQT12 devices when exposed to $10^{-3}$ mg TNT/mL IPA solution, output current were significantly increased, and similar observation was observed when P2 with 10 wt % PQT12 was exposed to $10^{-3}$ mg TNT/mL IPA solution.

Figure 14A:
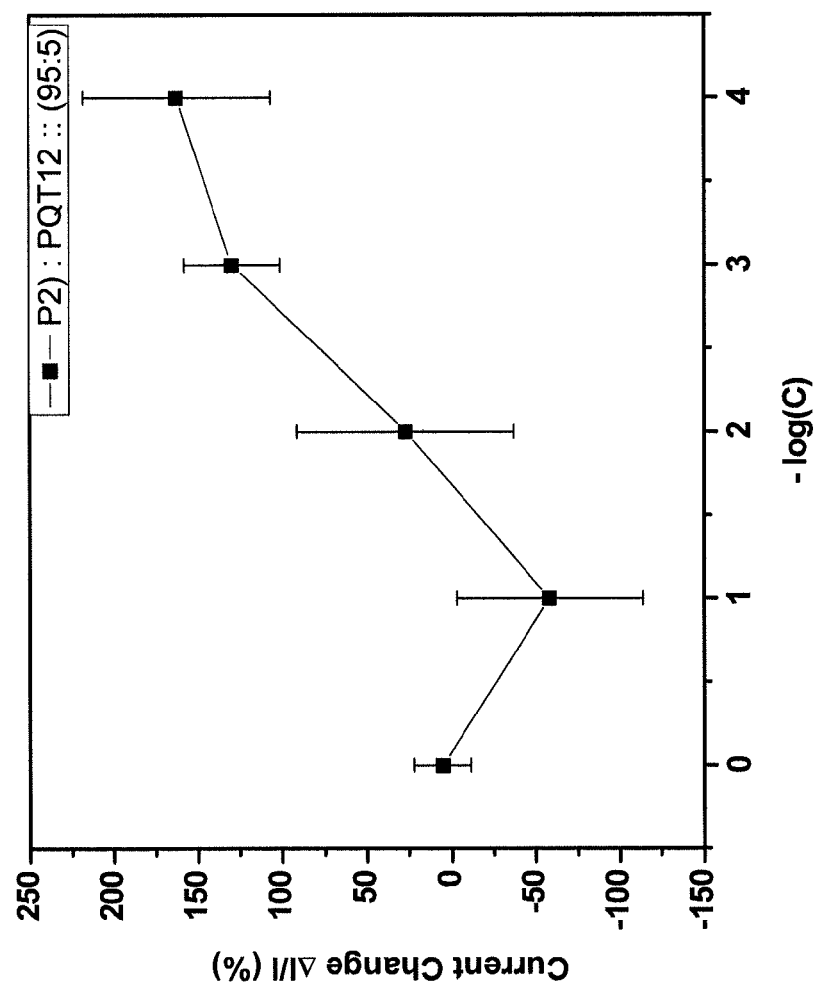
FIGS. 14A-14C show output curve current change $\Delta I/I$ (%) at $V_d=V_g=-100$ V of blended (a) P2:5% PQT12 device, (b) P2:10% PQT12 devices (c) 50-50% (P2:PQT12) blend exposed to the TNT solutions with various concentrations, (c) (to $10^{-4}$ mg TNT/mL IPA). Square shows mean value and bar shows standard deviation respectively.
Figure 14B:
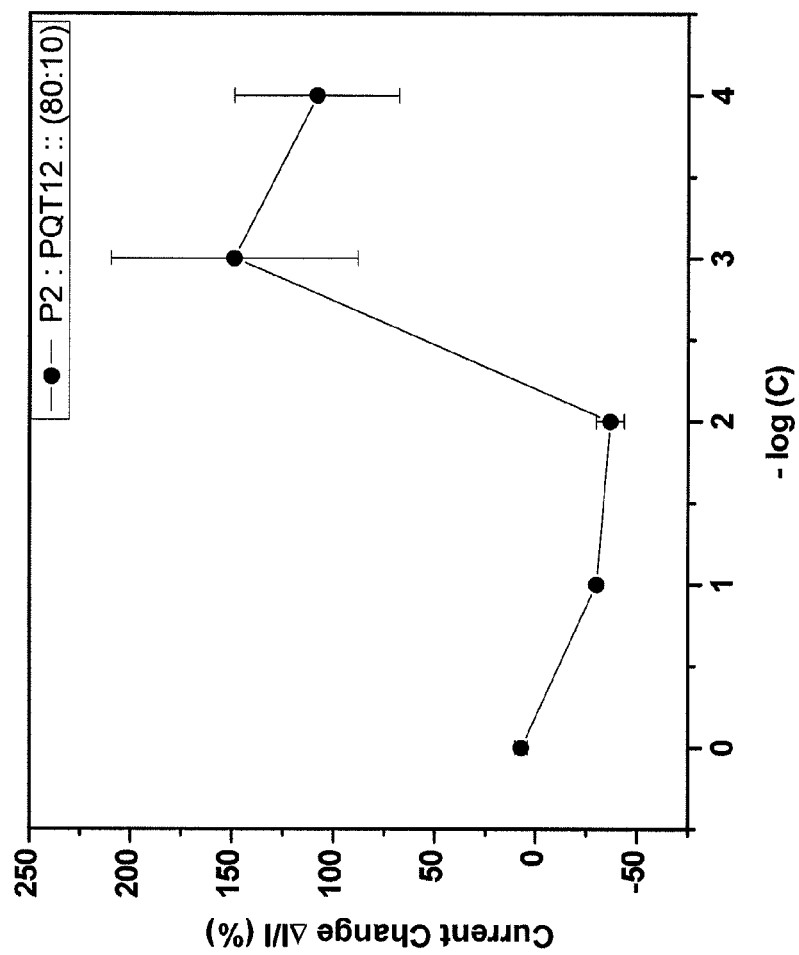
Figure 14C:
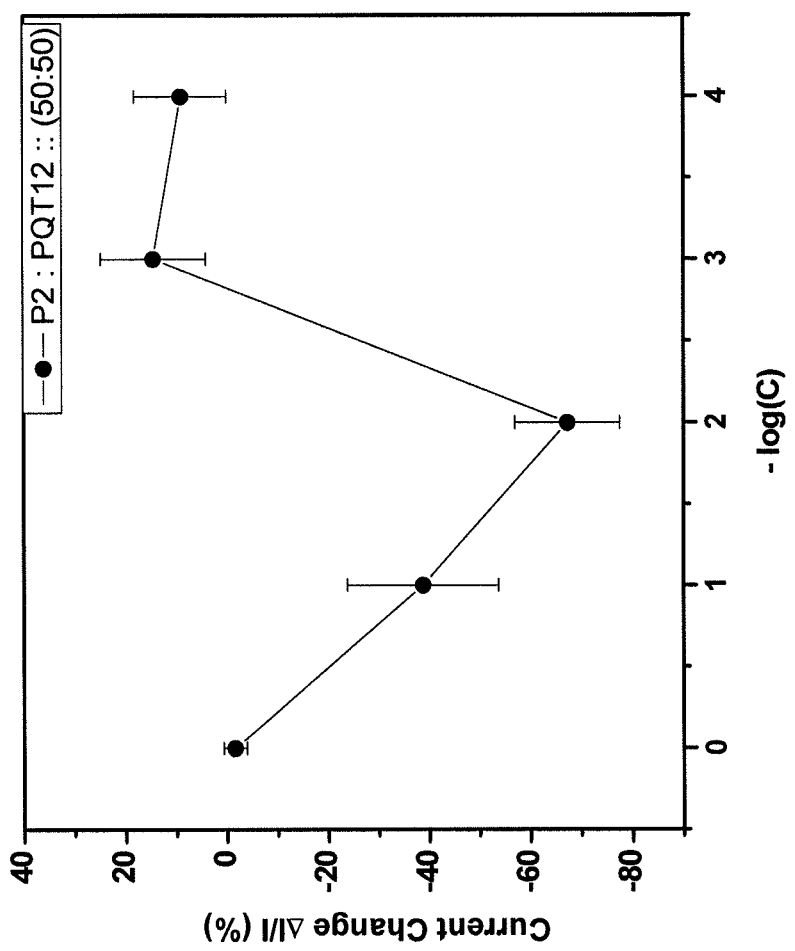
Figure 15A:
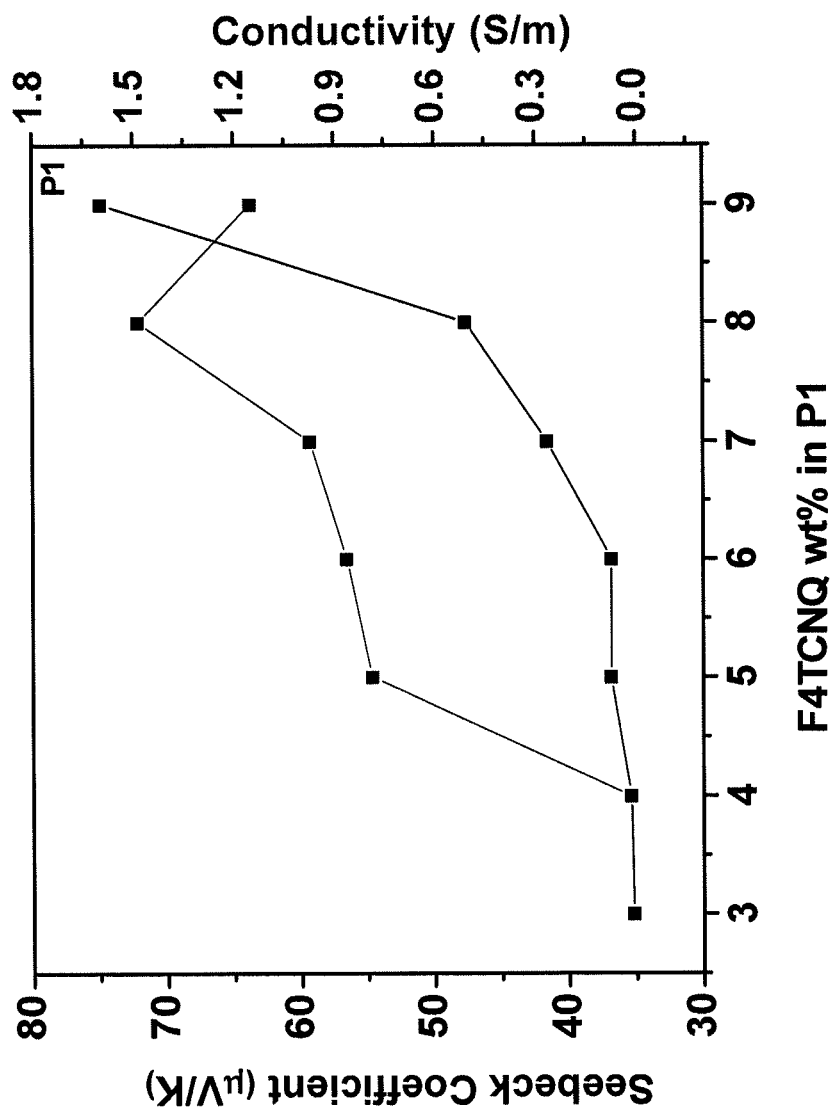
FIGS. 15A-15B provide plots of S and conductivity for P1 a) doped with different weight ratio of F4TCNQ, b) doped with NOPF$_6$ for prescribed time intervals.
Figure 15B:
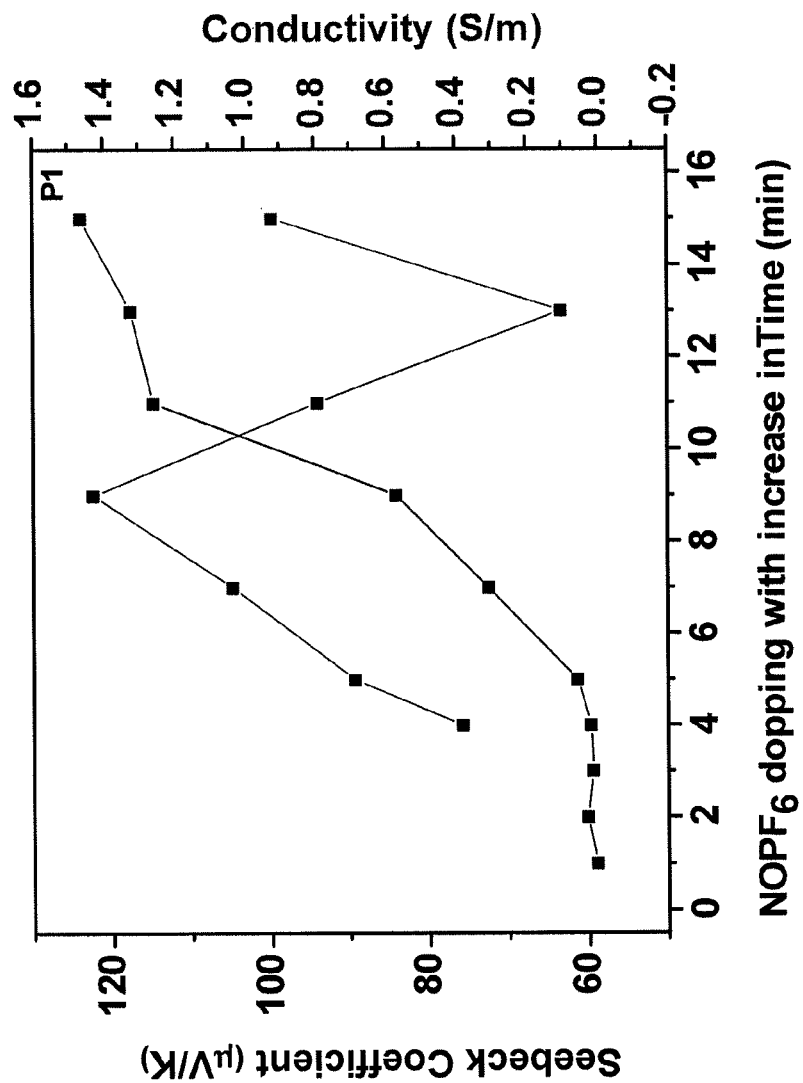
Figure 16A:
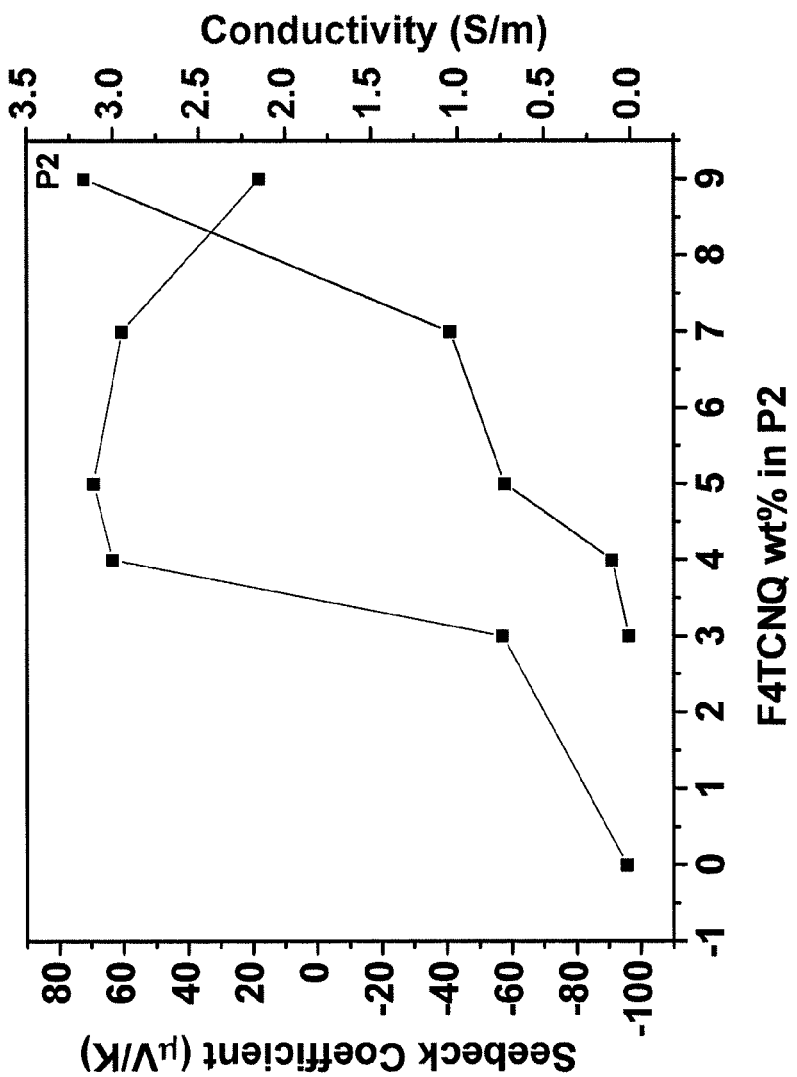
FIGS. 16A-16C provide plots of S and conductivity of a) P2 doped with different weight ratio of F4TCNQ b) P3 doped with different weight ratio of F4TCNQ c) P3 doped with NOPF$_6$ for the prescribed time interval. Power factor tables 4-8 are in FIG. 22.
Figure 16B:
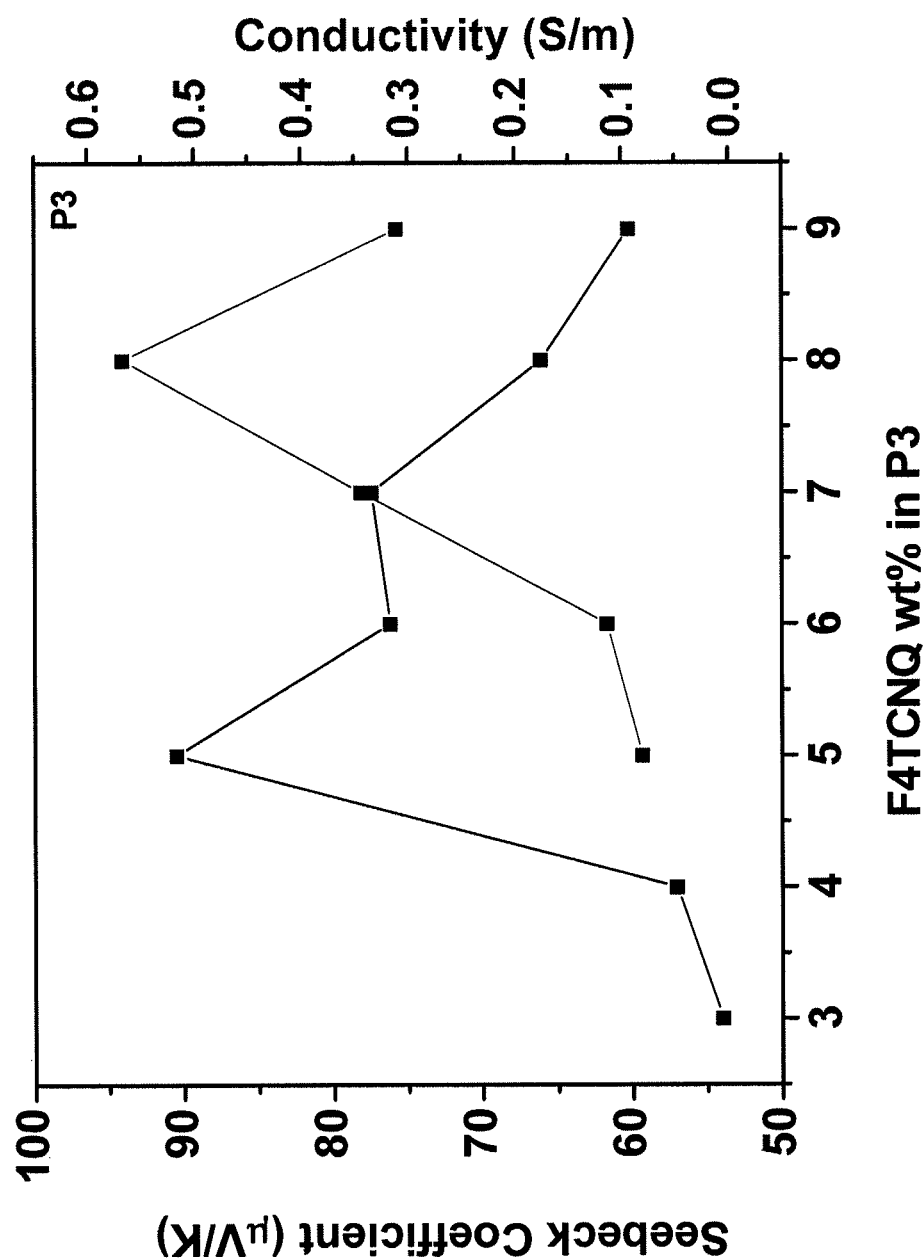
Figure 16C:
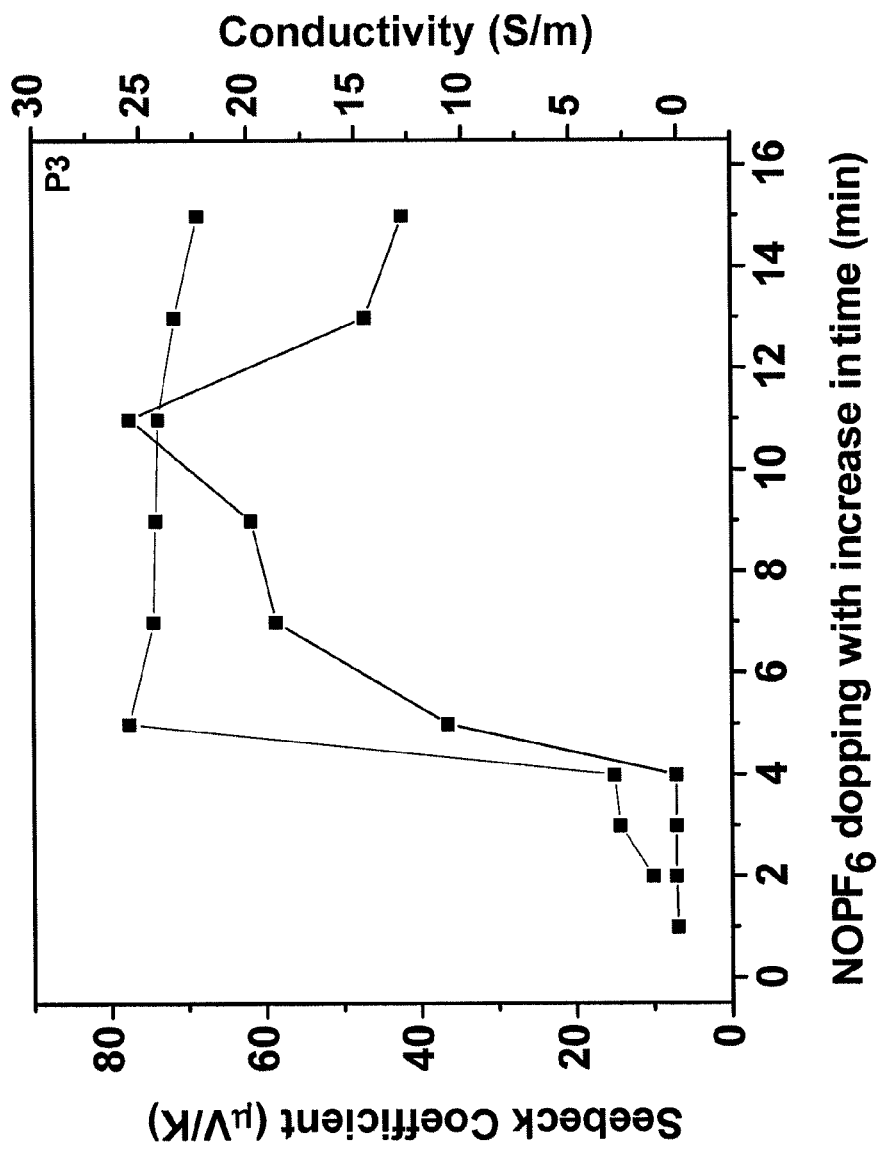

The P2:5% PQT12 blend device showed increased current on exposure to more dilute TNT solution ($10^4$ mg TNT/mL IPA), whereas the P2:10% PQT 12 showed decrease in the current on exposure to $10^{-4}$ mg TNT/mL IPA, as the TTF activity was relatively less. The P2:50% PQT12 blend device showed lowe r response to $>10^{-4}$ mg TNT/mL IPA (FIGS. 14A-14C). Thus, as was observed with TPT-TTF, the current increase was only observed for relatively dilute TNT solutions. Also, as was previously observed, a PQT12 film with essentially no TTF activity (the 95% PQT12 sample) showed current decreases in response to TNT at all the concentrations examined.

Conclusions

We demonstrated a preparation of a PQT12-type polymer with an additional thiophene inserted for grafting functional side chains. The side chains greatly decrease the homogeneity compared to PQT12 itself, but the use of the new copolymer blended with PQT12 allows retention of semiconducting properties while dispersing side chain groups. We used tetrathiafulvalene (TTF) as the primary functionality of interest. As expected, the TTF group acts as a hole trap, but this enabled a detrapping sensing mechanism for TNT to operate, and confirmed an effect we first found in a substituted TTF-PQT12 blend.

Experimental

Instrumentation and Methods. GPC was performed on 2×300 mm×7.8 mm Styragel HR4 columns in THF with Waters 2489 UV detector and filtered through a 0.2 µm filter before injection. A constant flow rate of 1 mL/min was used. Molecular weights were obtained relative to polystyrene standards for the polymer. $^1$H NMR and $^{13}$C spectra were recorded on Bruker Avance-400 MHz NMR spectrometer. Proton chemical shifts are expressed in parts per million ($\delta$) using TMS as an internal standard. The UV-vis spectra were recorded using a Cary 50 UV-vis spectrometer, corrected for baseline with a solvent-filled cuvette. CV was performed using an Autolab PGSTAT 302 potentiostat/galvanostat with a three-electrode cell in a 0.10 M solution of TBAP in acetonitrile at a scan rate of 100 mV/s. A film of the polymer was coated onto a Pt wire electrode by dipping the electrode into a solution containing the polymer. DSC measurement was performed using TA DSC Q20 modulated instrument at a heating and cooling rate of 5° C./min under $N_2$ atmosphere. XRD measurements were carried out on a Phillips X-pert pro X-ray diffraction system. The polymer film thickness was measured by using Keyence VK-X100 series Laser Microscope 3D and Profile Measurement. All the current-voltage (I-V) curves of devices were measured with an Agilent 4155C.

Materials. Tris(dibenzylideneacetone)dipalladium(0), Tri (o-tolyl)phosphine, 1,8-dibromooctane, N-methyl-N-phenylformamide, 1,8-Diazabicyclo[5.4.0]undec-7-ene (DBU), Tetrathiafulvalene, DMAP, anhydrous THF, DMF, Chlorobenzene, Diethyl ether, Lithium diisopropylamide solution (2 M in THF/heptane/ethylbenzene), $LiAlH_4$ (2M in THF) were purchased from Aldrich. All other chemicals were of reagent grade and used without further purification. 3,3'''-Didodecylquaterthiophene was obtained as reported in literature in 75% yield by Stille coupling of two equivalents of 2-bromododecylthiophene with 5,5'-bis(trimethyltin)-2,2'-bithiophene. [2,2'-bi(1,3-dithiolylidene)]-4-ylmethanol was synthesized as reported in literature, starting from tetrathiafulvalene.[74]

Fabrication of Field Effect Transistor Devices. Top gate/bottom contact OFETs were fabricated to investigate the charge transport properties of the copolymer and side chain functionalized copolymers under ambient condition. The devices were fabricated using highly n-doped <100> silicon wafers with 300 nm thermally grown oxide. The capacitance of the 300 nm $SiO_2$ gate insulator is 11.5 $nFcm^{-2}$. The wafers were then cleaned with piranha solution, sonicated in acetone and isopropanol, and then dried by forced nitrogen gas. Substrates were dried more thoroughly via 100° C. vacuum annealing for 20 minutes prior to a 2-hour exposure to hexamethyldisilazane (HMDS) vapor at 110° C. in a loosely sealed vessel. Cr/Au (3 nm/50 nm) electrode as source and drain electrodes were then thermally vapor-deposited through a shadow mask (channel width/length (W/L=32) at a rate of 0.3 Å/s. The substrate was then dipped in 0.001 mmol of 2,3,4,5,6-Pentafluorothiophenol in ethanol for 15 min followed by washing with ethanol and isopropanol and drying in oven for 30 min. The semiconducting films were deposited by spin coating 1.0 mg/mL of P1-P3 or blend system of P1 and P2 with PQT12 in chlorobenzene solution under ambient condition at 1500 rpm for 60 sec and kept in vacuum dessicator for 30 min prior to measurement.

All OFETs for TNT sensing were fabricated without any post-deposition annealing processes, to obtain a rougher surface for larger sensing area, which along with resistance from bottom contact interfaces, decreased the apparent mobility. Novec fluoropolymer was painted on the edge of the channel area to create a dam, followed by drop casting the TNT solution in IPA in the region bounded by the Novec (0.81 $cm^2$). Finally, IPA solvent was evaporated in air for 10 min. All sensing experiments were done in air.

Synthesis 2,2'-Dibromo-3,3'''-Didodecylquaterthiophene. To the solution of 0.25 g (0.37 mmol) of 3,3'''-Didodecylquaterthiophene in 5 mL of chloroform and 5 mL of acetic acid was added 0.15 g (0.84 mmol) of NBS. The solution was kept for stirring for 2 h. The resulting mixture was poured into 10 mL of water and extracted twice from 20 mL of ethyl acetate. The combined organic layer was dried over $Na_2SO_4$ and concentrated under reduced pressure to yield orange solid. The crude product was purified by silica gel column chromatography by eluting with hexane to obtain yellow solid.

Yield: 89%. Lit m.p. 76° C., $^1$H NMR (400 MHz $CDCl_3$): $\delta$ 0.87 (t, 6H, J=6.38 Hz), 1.25-1.38 (m, 36H), 1.60 (m, 4H), 2.71 (t, 4H, J=7.57 Hz), 6.89 (s, 2H), 6.96 (d, 2H, J=3.83 Hz), 7.10 (d, 2H, J=3.83 Hz). $^{13}$C NMR (100 MHz, $CDCl_3$): $\delta$ 14.37, 22.94, 29.43, 29.61, 29.64, 29.81, 29.90, 29.93, 30.75, 32.17, 110.89, 124.23, 127.19, 131.94, 132.95, 134.31, 137.27, 140.77.

Thiophen-3-ylmethanol. To the solution of 6.4 g (57.06 mmol) of thiophene-3-carbaldehyde in 8 mL of anhydrous THF was added 31 mL of $LiAlH_4$ (2 M in THF) slowly. The solution was stirred for 1 h. The resulting mixture was dropwise poured into 500 mL of water and extracted twice from 200 mL of methylene chloride. The combined organic layer was dried over $Na_2SO_4$ and concentrated under reduced pressure to yield pale yellow liquid. The crude product was purified by silica gel column chromatography by eluting with ethyl acetate to obtain colorless liquid. Yield: 72%. $^1$H NMR (400 MHz $CDCl_3$): $\delta$ 1.80 (s, 1H), 4.68 (s, 2H), 7.08 (d, 1H, J=4.34 Hz), 7.22 (s, 1H), 7.31 (d, 1H, J=2.48 Hz). $^{13}$C NMR (100 MHz, $CDCl_3$): $\delta$ 60.52, 121.99, 126.31, 126.94, 142.39.

Thiophen-3-ylmethyl acetate. To the solution of 0.44 g (3.8 mmol) of Thiophen-3-ylmethanol in 5 mL anhydrous methylene chloride was added 0.58 mL (4.18 mmol) of anhydrous triethylamine and kept for stirring under nitrogen atmosphere. To the solution was then added 0.01 g (0.09 mmol) of DMAP followed by the addition of 0.29 mL (4.17 mmol) acetyl chloride dropwise and kept for stirring for 3 h under nitrogen atmosphere. The resulting mixture was poured into 50 mL of water and extracted twice from 70 mL of methylene chloride. The combined organic layer was dried over $Na_2SO_4$ and concentrated under reduced pressure to yield pale yellow liquid. The crude product was purified by silica gel column chromatography by eluting with hexane and ethyl acetate (1:1) to obtain colorless liquid. Yield: 85%. $^1$H NMR (400 MHz CDCl$_3$): δ 2.08 (s, 3H), 5.11 (s, 2H), 7.09 (s, 1H), 7.31 (m, 2H). $^{13}$C NMR (100 MHz, CDCl$_3$): δ 20.78, 61.13, 124.28, 126.15, 127.55, 136.82, 170.56.

4-(((8-bromooctyl)oxy)methyl)-2,2'-bi(1,3-dithiolylidene). To a suspension of 0.05 g (2.16 mmol) of NaH (60% in mineral oil) in 5 mL anhydrous THF, a solution of 0.2 g (0.87 mmol) of [2,2'-bi(1,3-dithiolylidene)]-4-ylmethanol in 1 mL anhydrous THF was added dropwise under nitrogen atmosphere followed by the addition of 1 mL of anhydrous DMF. The resulting mixture was stirred for half an hour. Then to the mixture 0.8 g (2.9 mmol) of 1,8-dibromooctane was added dropwise. The mixture was stirred for 48 h under nitrogen atmosphere. The reaction mixture was poured then into 100 mL water and extracted 3-4 times from 40 mL methylene chloride. The combined organic layer was dried over $Na_2SO_4$ and concentrated under reduced pressure to yield pale yellow liquid. The crude product was purified by silica gel column chromatography by eluting with hexane and ethyl acetate (1:1) to obtain colorless liquid. Yield: 65%. $^1$H NMR (400 MHz CDCl$_3$): δ 1.25-1.88 (m, 12H), 3.40 (t, 2H, J=7.13 Hz), 3.42 (t, 2H, J=6.93 Hz), 4.21 (s, 2H), 6.17 (s, 1H), 6.30 (s, 2H): $^{13}$C NMR (100 MHz, CDCl$_3$): δ 26.18, 28.34, 28.91, 29.41, 29.73, 33.03, 34.29, 68.15, 70.55, 114.69, 115.94, 119.21, 119.35, 135.30.

Polymerization. A mixture of 0.5 mg (0.002 mmol) Pd(OAc)$_2$, 3.7 mg (0.036 mmol) pivalic acid, 43.5 mg (0.31 mmol) K$_2$CO$_3$, 100 mg (0.12 mmol) 2,2'-Dibromo-3,3'''-Didodecylquaterthiophene, and 18.9 mg (0.12 mmol) Thiophen-3-ylmethyl acetate was stirred in 2 mL anhydrous dimethylacetamide for 3 h at 100° C. under nitrogen atmosphere. The reaction mixture was poured into an aqueous solution of ethylenediaminetetraacetic acid disodium salt (pH=8) and the obtained suspension was stirred overnight at room temperature. The precipitate was separated by filtration and washed with 0.5 N HCl solution. The precipitate was dissolved in CHCl$_3$, and reprecipitated in methanol. The copolymer was then purified by soxhlet extraction, first with methanol then with hexane and finally with chloroform to yield pure polymer. Yield: 90%. Mn=10772, Mw/Mn=2.89. $^1$H NMR (400 MHz, CDCl$_3$): δ 1.03 (b, 6H), 1.27-1.69 (b, 40H), 2.16 (b, 1H), 2.79 (b, 4H), 5.21 (b, 2H), 7.05 (b, 4H), 7.15 (b, 3H).

Postfunctionalization of P1. To the solution of 37 mg (0.047 mmol) of P1 dissolved in 3 mL of anhydrous THF was added 0.9 mg (0.037 mmol) of NaH (60% in mineral oil) and stirred for half an hour under nitrogen atmosphere. Then to the mixture a solution of 20 mg (0.048 mmol) 4-(((8-bromooctyl)oxy)methyl)-2,2'-bi(1,3-dithiolylidene)/propargyl bromide in 0.2 mL of anhydrous THF was added followed by the addition of DBU (2 μL) in catalytic amount. The mixture was stirred for 48 h under nitrogen atmosphere. The reaction mixture was poured then into 100 mL water and extracted 3-4 times from 40 mL methylene chloride. The combined organic layer was dried over $Na_2SO_4$ and concentrated under reduced pressure to yield red solid. The solid was then dissolved in CHCl$_3$, and reprecipitated in methanol 3-4 times. The polymer was then purified by washing it with hexane and methanol, followed by reprecipitating it again in methanol. The solid hence obtained was then dried under vacuum for 24 h. P2: Yield: 66%. Mn=11857, Mw/Mn=2.2. $^1$H NMR (400 MHz, CDCl$_3$): δ 0.79 (b, 6H), 0.96-1.55 (b, 52H), 2.34 (b, 2H), 2.58 (b, 2H), 3.18 (b, 2H), 3.25 (b, 2H), 3.76 (b, 2H), 3.88 (b, 2H), 5.81 (b, 1H), 5.94 (b, 2H), 6.69-6.95 (b, 7H). P3: Yield: 80%. Mn=12228, Mw/Mn=2.41. $^1$H NMR (400 MHz, CDCl$_3$): δ 0.87 (b, 6H), 1.26-1.69 (b, 40H), 2.51 (b, 1H), 2.77 (b, 4H), 4.28 (b, 2H), 4.70 (b, 2H), 7.07 (b, 4H), 7.14 (b, 3H).

References for Example 2
(1) Forrest, S. R. *Nature* 2004, 428, 911.
(2) Facchetti, A. *Mater. Today* 2007, 10, 28.
(3) Gunes, S.; Neugebauer, H.; Sariciftci, N. S. *Chem. Rev.* 2007, 107, 1324.
(4) Arias, A. C.; MacKenzie, J. D.; McCulloch, I.; Rivnay, J.; Salleo, A. *Chem. Rev.* 2010, 110, 3.
(5) Friend, R. H.; Gymer, R. W.; Holmes, A. B.; Burrougher, J. H.; Marks, R. N.; Taliani, C.; Bradley, D. D.C.; Dos Santos, D. A.; Bredas, J. L.; Logdlund, M.; Salaneck, W. R. *Nature* 1999, 397, 121.
(6) Lo, S.C.; Burn, P. L.; *Chem. Rev.* 2007, 107, 1097.
(7) Dimitrakopoulos, C. D.; Malenfant, P. R. L. *Adv. Mater.* 2002, 14, 99.
(8) Wen, Y.; Liu, Y. *Adv. Mater.* 2010, 22, 1331.
(9) Cheng, Y.-J.; Yang, S.-H.; Hsu, C.-S. *Chem. Rev.* 2009, 109, 5868.
(10) Thompson, B. C.; Frechet, J. M. J. *Angew. Chem., Int. Ed.* 2008, 47, 58.
(11) McQuade, D. T.; Pullen, A. E.; Swager, T. M. *Chem. Rev.* 2000, 100, 2537.
(12) Du, Y.; Shen, S. Z.; Kefeng, C.; Casey, P. S. *Pro. Polym. Sci.* 2012, 37, 820.
(13) Osaka, I.; McCullough, R. D. *Acc. Chem. Res.* 2008, 41, 1202.
(14) Beaujuge, P. M.; Frechet, J. M. *J. Am. Chem. Soc.* 2011, 133, 20009.
(15) Mishra, A.; Ma, C.-Q.; Bauerle, P. *Chem. Rev.* 2009, 109, 1141.
(16) Skotheim, T. A.; Reynolds, J. *Conjugated Polymers: theory, Synthesis, Properties, and Characterization*, 3$^{rd}$ ed.; Blanchard, P.; Leriche, P.; Frere, P.; Roncali, J., Taylor & Francis Group, 2006.
(17) Purcell, S. T.; Garicia, N.; Binh, V. T.; Jones, L.; II; Tour, J. M. *J. Am. Chem. Soc.* 1994, 116, 11985.
(18) Tour, J. M; Jones, L.; Pearson, D. L.; Lamba, J. J. S.; Burgin, T. P.; Whitesides, G. M.; Allara, D. L.; Parikh, A. N.; Atre, S. V. *J. Am. Chem. Soc.* 1995, 117, 9529.
(19) Liedberg, B.; Yang, Z.; Engquist, I.; Wirde, M.; Gelius, U.; Gotz, G.; Bauerle, P.; Rummel, R. M.; Ziegler, C.; Gopel, W. *J. Phys. Chem. B* 1997, 101, 5951.
(20) Taniguchi, S.; Minamoto, M.; Matsushita, M. M.; Sugawara, T.; Kawada, Y.; Bethell, D. *J. Mater. Chem.* 2006, 16, 3459.
(21) Huang, W.; Masuda, G.; Maeda, S.; Tanaka, H.; Ogawa, T. *Chem-Eur J.* 2006, 12, 607.
(22) Barik, S.; Valiyaveettil, S. *Macromolecules* 2008, 41, 6376.
(23) Olenyuk, B.; Whiteford, J. A.; Fechtenkotter, A.; Stang, P. J. *Nature* 1999, 398, 796.
(24) Nie, Z.; Fava, D.; Kumacheva, E.; Zou, S.; Walker, G. C.; Rubinstein, M. *Nat. Mater.* 2007, 6, 609.
(25) (a) Lu, S.; Liu, T.; Ke, L.; Ma, D. G.; Chua, S. J.; Huang, W. *Macromolecules* 2005, 38, 8494. (b) Zahn, S.; Swager, T. M. *Angew. Chem., Int. Ed.* 2002, 41, 4225. (c) Lee, M.; Cho, B. K.; Zin, W. C. *Chem. Rev.* 2001, 101, 2869.
(26) Roncali, J.; Li, H. S.; Garreau R.; Garnier, F.; Lemaire, M. *Synth. Met.* 1990, 36, 267.
(27) Bauerle, P.; Scheib, S. *Adv. Mater.* 1993, 5, 848.
(28) Bauerle, P.; Gotz, G.; Hiller, M.; Scheib, S.; Fischer, T.; Segelbacher, U.; Bennati, M.; Grupp, A.; Mehring, M.; Stoldt, M.; Seidel, C.; Geiger, F.; Schweizer, H.; Umbach, E.; Schmelzer, M.; Roth, S.; Egelhaaf, H. J.; Oelkrug, D.; Emele, P.; Port, H. *Synth. Met.* 1993, 61, 71.
(29) Scheib, S.; Bauerle, P. *J. Mater. Chem.* 1999, 9, 2139.
(30) Marsella, M. J.; Swager, T. M. *J. Am. Chem. Soc.* 1993, 115, 12214. (b) Swager, T. M.; Marsella, M. J. *Adv. Mater.* 1994, 6, 595. (c) Swager, T. M.; Marsella, M. J.; Bicknell, L. K.; Zhou, Q. *Polym. Prep.* 1994, 35, 206.
(31) Vigalok, A.; Zhu, Z.; Swager, T. M. *J. Am. Chem. Soc.* 2001, 123, 7917.
(32) Ballarin, B.; Masiero, S.; Seeber, R.; Tonelli, D. *J. Electroanal. Chem.* 1998, 449, 173.
(33) Li, Y.; Vamvounis, G.; Holdcroft, S. *Macromolecules* 2002, 35, 6900.
(34) Kong, H.; Jung, B. J.; Sinha, J.; Katz, H. E. *Chem. Mater.* 2012, 24, 2621.
(35) Huang, J.; Dawidczyk, T. J.; Jung, B. J.; Sun, J.; Mason, A. F.; Katz, H. E. *J. Mater. Chem.* 2010, 20, 2644.
(36) Royer, J. E.; Lee, S.; Chen, C.; Aim, B.; Trogler, W. C.; Kanicki, J.; Kummel, A. C. *Sens. Actuat. B* 2011, 158, 333.
(37) Zhu, Z. T.; Mason, J. T.; Dieckmann, R.; Malliaras, G. G. *Appl. Phys. Lett.* 2002, 81, 4643.
(38) Li, D. W.; Borkent, E. J.; Nortrup, R.; Moon, H.; Katz, H.; Bao, Z. N. *Appl. Phys. Lett.* 2005, 86, 042105.
(39) Crone, B.; Dodabalapur, A.; Gelperin, A.; Torsi, L.; Katz, H. E.; Lovinger, A. J.; Bao, Z. *Appl. Phys. Lett.* 2001, 78, 2229.
(40) Chang, J. B.; Liu, V.; Subramanian, V.; Sivula, K.; Luscombe, C.; Murphy, A.; Liu, J. S.; Frechet, J. M. J. *J. Appl. Phys.* 2006, 100, 014506.
(41) Tremblay, N. J.; Jung, B. J.; Breysse, P.; Katz, H. E. *Adv. Funct. Mater.* 2011, 21 4314.
(42) Sun, J.; Yeh, M.-L.; Jung, B. J.; Zhang, B.; Feser, J.; Majumdar, A.; Katz, H. E. *Macromolecules* 2010, 43, 2897.
(43) Poehler, T. O.; Katz, H. E. *Energy Environ. Sci.* 2012, 5, 8110.
(44) Dubey, N.; Leclerc, M. *J. Polym. Sci. Part B: Polym. Phys.* 2011, 49, 467.
(45) Zuzok, R.; Kaiser, A. B.; Pukacki, W.; Roth, S. *J. Chem. Phys.* 1991, 95, 1270.
(46) Park, Y. W. *Synth. Met.* 1991, 45, 173.
(47) Park, Y. W.; Yoon, C. O.; Lee, C. H.; Shirakawa, H.; Suezaki, Y.; Akagi, K. *Synth. Met.* 1991, 41, 27.
(48) Pukacki, W.; Plocharski, J.; Roth, S. *Synth. Met.* 1994, 62, 253.
(49) Mateeva, N.; Niculescu, H.; Schlenoff, J.; Testardi, L. R. *J. Appl. Phys.* 1998, 83, 3111.
(50) Yan, H.; Sada, N.; Toshima, N. *J. Therm. Anal. Calorim.* 2002, 69, 881.
(51) Toshima, N. *Macromol. Symp.* 2002, 186, 81.
(52) Yakuphanoglu, F.; Senkal, B. F. *J. Phys. Chem. C* 2007, 111, 1840.
(53) Carrasco, P. M.; Cortazar, M.; Ochoteco, E.; Calahorra, E.; Pomposo, J. A. *Surf. Interface Anal.* 2007, 39, 26.
(54) Kemp, N. T.; Kaiser, A. B.; Liu, C.-J.; Chapman, B.; Mercier, O.; Carr, A. M.; Trodahl, H. J.; Buckley, R. G.; Partridge, A. C.; Lee, J. Y.; Kim, C. Y.; Bartl, A.; Dunsch, L.; Smith, W. T.; Shapiro, J. S. *J. Polym. Sci. Part B: Polym. Phys.* 1999, 37, 953.
(55) Maddison, D. S.; Unsworth, *J. Synth. Met.* 1988, 26, 99.
(56) Hiroshige, Y.; Ookawa, M.; Toshima, N. *Synth. Met.* 2006, 156, 1341.
(57) Hiroshige, Y.; Ookawa, M.; Toshima, N. *Synth. Met.* 2007, 157, 467.
(58) Aich, R. B.; Blouin, N.; Bouchard, A.; Leclerc, M. *Chem. Mater.* 2009, 21, 751.
(59) Levesque, I.; Bertrand, P. O.; Blouin, N.; Leclerc, M.; Zecchin, S.; Zotti, G.; Ratcliffe, C. I.; Klug, D. D.; Gao, X.; Gao, F.; Tse, J. S. *Chem. Mater.* 2007, 19, 2128.
(60) Wakim, S.; Aich, R. B., Tao, Y.; Leclerc, M. *Polym. Rev.* 2008, 48, 432.
(61) Blouin, N.; Leclerc, M.; Vercelli, B.; Zecchin, S.; Zotti, G. *Macromol. Chem. Phys.* 2006, 207, 175.
(62) Xuan, Y.; Liu, X.; Desbief, S.; Lecle're, P.; Fahlman, M.; Lazzaroni, R.; Berggren, M.; Cornil, J.; Emin, D.; Crispin, X. *Phys. Rev. Part B* 2010, 82, 115454.
(63) Lu, B.-Y.; Liu, C.-C.; Lu, S.; Xu, J.-K.; Jiang, F.-X.; Li, Y.-Z.; Zhang, Z. *Chin. Phys. Lett.* 2010, 27, 057201.
(64) Masubuchi, S.; Kazama, S.; Mizoguchi, K.; Honda, M.; Kume, K.; Matsushita, R.; Matsuyama, T. *Synth. Met.* 1993, 57, 4962.
(65) Magnoni, M. C.; Gallazzi, M C.; Zerbi, G. *Acta. Polym.* 1996, 47, 228.
(66) Bryce, M. R.; Chissel, A. D.; Gopal, J.; Kathirgamanathan, P.; Parker, D. *Synth. Met.* 1991, 39, 397.
(67) Gautier, C.-T.; Gorgues, A.; Jubault, M.; Roncali, J. *Macromolecules* 1993, 26, 4094.
(68) Huchet, L.; Akoudad, S.; Levillain, E.; Roncali, J.; Emge, A.; Bauerle, P. *J. Phys. Chem. B* 1998, 102, 7776.
(69) Huchet, L.; Akoudad, S.; Roncali, J. *Adv. Mater.* 1998, 10, 541.
(70) Besbes, M.; Trippe, G.; Levillain, E.; Mazari, M.; Derf, F. L.; Perepichka, I. F.; Derdour, A.; Gorgues, A.; Salle', M.; Roncali, J. *Adv. Mater.* 2001, 13, 1249.
(71) Lyskawa, J.; Derf, F. L.; Levillain, E; Mazari, M.; Salle', M.; Dubois, L.; Viel, P.; Bureau, C.; Palacin. S. *J. Am. Chem. Soc.* 2004, 126, 12194.
(72) N. Miyaura in *Cross-Coupling Reactions—A Practical Guide Topics in Current Chemistry*, Vol. 219 (Ed: N. Miyaura), Springer, Berlin, 2002, p. 11-59.
(73) Brem, J.; Liljeblad, A.; Paizs, C.; Tosa, M. I; Irimie, D. F.; Kanerva, L. T. *Tet Asymmetry* 2011, 22, 315.
(74) Garin, J.; Orduna, J.; Uriel, S.; Moore, A. J.; Bryce, M. R.; Wegener, S.; Yufit, D. S.; Howard, J. A. K. *Synthesis* 1994, 5, 489.
(75) Fujinami, Y.; Kuwabara, J.; Lu, W.; Hayashi, H.; Kanbara, T. *ACS Macro. Lett.* 2012, 1, 67.
(76) He, Y.; Wu, W.; Zhao, G.; Liu, Y.; Li, Y. *Macromolecules* 2008, 41, 9760.
(77) (a) Bryce, M. R.; Murphy, L. C. *Nature* 1984, 309, 119. (b) Aziz, E. F.; Vollmer, A.; Eisebitt, S.; Eberhardt, W.; Pingel, P.; Neher, D.; Koch, N. *Adv. Mater.* 2007, 19, 3257.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. An electro-chemical sensor, comprising:
   a first electrode;
   a second electrode spaced apart from said first electrode; and
   a semiconductor channel in electrical contact with said first and second electrodes,
   wherein said semiconductor channel comprises a trapping material,
   wherein said trapping material reduces an ability of said semiconductor channel to conduct a current of charge carriers by trapping at least some of said charge carriers to localized regions within said semiconductor channel,
   wherein said semiconductor channel comprises at least a portion configured to be exposed to an analyte to be detected, and
   wherein said trapping material, when exposed to said analyte, interacts with said analyte so as to at least partially restore the ability of said semiconductor channel to conduct said current of charge carriers.

2. An electro-chemical sensor according to claim 1, wherein said semiconductor channel comprises a p-type semiconductor such that said charge carriers are holes,
   wherein said trapping material is an electron donor material, and
   wherein said analyte is an electron acceptor material.

3. An electro-chemical sensor according to claim 1, wherein said semiconductor channel comprises an n-type semiconductor such that said charge carriers are electrons,
   wherein said trapping material is an electron acceptor material, and
   wherein said analyte is an electron donor material.

4. An electro-chemical sensor according to claim 1, wherein said semiconductor channel comprises an organic semiconductor.

5. An electro-chemical sensor according to claim 4, wherein said trapping material is dispersed within said organic semiconductor.

6. An electro-chemical sensor according to claim 5, wherein said trapping material is an organic material.

7. An electro-chemical sensor according to claim 4, wherein said organic semiconductor is an organic polymer semiconductor.

8. An electro-chemical sensor according to claim 7, wherein said trapping material is covalently attached to said organic polymer semiconductor.

9. An electro-chemical sensor according to claim 1, further comprising a third electrode arranged proximate said semiconductor channel to expose at least a portion to said semiconductor channel to a controllable electric field such that said first, second and third electrodes and said semiconductor channel together provide a field effect transistor.

10. An electro-chemical sensor according to claim 9, further comprising a dielectric layer disposed between said third electrode and said semiconductor channel.

11. An electro-chemical sensor according to claim 1, further comprising a flexible substrate upon which said semiconductor channel, said first electrode, and said second electrode are formed.

12. An electro-chemical sensor array comprising a plurality of electro-chemical sensor elements, wherein at least one electro-chemical sensor element of said plurality of electro-chemical sensor elements comprises:
   a first electrode;
   a second electrode spaced apart from said first electrode; and
   a semiconductor channel in electrical contact with said first and second electrodes,
   wherein said semiconductor channel comprises a trapping material,
   wherein said trapping material reduces an ability of said semiconductor channel to conduct a current of charge carriers by trapping at least some of said charge carriers to localized regions within said semiconductor channel,
   wherein said semiconductor channel comprises at least a portion configured to be exposed to an analyte to be detected, and
   wherein said trapping material, when exposed to said analyte, interacts with said analyte so as to at least partially restore the ability of said semiconductor channel to conduct said current of charge carriers.

13. An electro-chemical sensor array according to claim 12, wherein said trapping material of a first electro-chemical sensor element of said plurality of electro-chemical sensor elements interacts with a first analyte,
   wherein a trapping material of a second electro-chemical sensor element of said plurality of electro-chemical sensor elements interacts with a second analyte,
   wherein said first trapping material is different from said second trapping material, and
   wherein said first analyte is different from said second analyte.

14. An electro-chemical sensor array according to claim 12, wherein at least a second electro-chemical sensor element of said plurality of electro-chemical sensor elements comprises:
   a first electrode;
   a second electrode spaced apart from said first electrode; and
   a semiconductor channel in electrical contact with said first and second electrodes,
   wherein said analyte that interacts with said trapping material of the first mentioned electro-chemical sensor element interacts with said semiconductor channel of said second electro-chemical sensor element so as to decrease an ability of said semiconductor channel of said second electro-chemical sensor element to conduct a current of charge carriers.

15. An electro-chemical sensor array according to claim 14, wherein a semiconducting material of said first electro-chemical sensor element and a semiconducting material of said second electro-chemical sensor element are substantially the same material and said semiconductor channel of said second electro-chemical sensor element is substantially free of trapping material.

16. An electrical circuit comprising an electro-chemical sensor element, wherein said electro-chemical sensor element comprises:
   a first electrode;
   a second electrode spaced apart from said first electrode; and
   a semiconductor channel in electrical contact with said first and second electrodes,
   wherein said semiconductor channel comprises a trapping material,
   wherein said trapping material reduces an ability of said semiconductor channel to conduct a current of charge carriers by trapping at least some of said charge carriers to localized regions within said semiconductor channel,
   wherein said semiconductor channel comprises at least a portion configured to be exposed to an analyte to be detected, and wherein said trapping material, when exposed to said analyte, interacts with said analyte so as to at least partially restore the ability of said semiconductor channel to conduct said current of charge carriers.

17. An electrical circuit according to claim 16, further comprising an electronic element that remains unaffected by exposure of said at least a portion of said electronic circuit to said analyte.

18. An electrical circuit according to claim 16, further comprising a second electro-chemical sensor element comprising:
   a first electrode;
   a second electrode spaced apart from said first electrode; and
   a semiconductor channel in electrical contact with said first and second electrodes,
   wherein said analyte that interacts with said trapping material of the first mentioned electro-chemical sensor element interacts with said semiconductor channel of said second electro-chemical sensor element so as to decrease an ability of said semiconductor channel of said second electro-chemical sensor element to conduct a current of charge carriers.

19. The electrical circuit according to claim 18, further comprising an inverter.

* * * * *